United States Patent
Vanotti et al.

(10) Patent No.: US 7,279,575 B2
(45) Date of Patent: Oct. 9, 2007

(54) PYRIMIDYLPYRROLE DERIVATIVES ACTIVE AS KINASE INHIBITORS

(75) Inventors: Ermes Vanotti, Milan (IT); Roberto D'Alessio, Milan (IT); Marcellino Tibolla, Milan (IT); Mario Varasi, Milan (IT); Alessia Montagnoli, Milan (IT); Corrado Santocanale, Como (IT); Paolo Orsini, Milan (IT); Antonio Pillan, Milan (IT)

(73) Assignee: Pfizer Italia S.r.l., Rome (IT)

( * ) Notice: Subject to any disclaimer, the term of this patent is extended or adjusted under 35 U.S.C. 154(b) by 507 days.

(21) Appl. No.: 10/912,319

(22) Filed: Aug. 5, 2004

(65) Prior Publication Data

US 2005/0043323 A1 Feb. 24, 2005

Related U.S. Application Data

(60) Provisional application No. 60/580,837, filed on Jun. 18, 2004, provisional application No. 60/493,633, filed on Aug. 8, 2003.

(51) Int. Cl.
*C07D 239/02* (2006.01)
*A01N 43/54* (2006.01)
*A61K 31/505* (2006.01)

(52) U.S. Cl. .................. 544/294; 514/256; 514/275

(58) Field of Classification Search .................. None
See application file for complete search history.

(56) References Cited

OTHER PUBLICATIONS

*Current Opinion in Chemical Biology 1999*, 3, 459-465.
Montagnoli et al., *EMBO Journal*, 21 (12), 3171-3181 (2002).

*Primary Examiner*—Cecilia Tsang
*Assistant Examiner*—Timothy P Thomas
(74) *Attorney, Agent, or Firm*—Scully, Scott, Murphy & Presser, P.C.

(57) ABSTRACT

Pyrimidylpyrrole derivatives of formula (I) and pharmaceutically acceptable salts thereof, as defined in the specification, process for their preparation and pharmaceutical compositions comprising them are disclosed; the compounds of the invention may be useful, in therapy, in the treatment of diseases associated with a disregulated protein kinase activity, like cancer.

12 Claims, No Drawings

PYRIMIDYLPYRROLE DERIVATIVES ACTIVE AS KINASE INHIBITORS

CROSS REFERENCE TO RELATED APPLICATIONS

The present application claims benefit of U.S. Provisional Application No. 60/580,837 filed Jun. 18, 2004 and U.S. Provisional Application No. 60/493,633 filed Aug. 8, 2003.

BACKGROUND OF THE INVENTION

1. Field of the Invention

The present invention relates to pyrimidylpyrrole derivatives, to a process for their preparation, to pharmaceutical compositions comprising them, and to their use as therapeutic agents, particularly in the treatment of cancer and cell proliferation disorders.

2. Discussion of the Background

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

Among the several protein kinases known in the art as being implicated in the growth of cancer cells is Cdc7, an evolutionary conserved serine-threonine kinase which plays a pivotal role in linking cell cycle regulation to genome duplication, being essential for the firing of DNA replication origins (see Montagnoli A. et al., EMBO Journal, Vol. 21, No. 12, pp. 3171-3181, 2002).

SUMMARY OF THE INVENTION

It is an object of the invention to provide compounds which are useful, in therapy, as agents against a host of diseases caused by and/or associated to a disregulated protein kinase activity and, more particularly, Cdk2 and Cdc7 activity.

It is another object to provide compounds, which are endowed with protein kinase inhibiting activity and, more particularly, Cdk2 and Cdc7 inhibiting activity.

The present inventors have now discovered that some pyridylpyrroles, and derivatives thereof, are endowed with protein kinase inhibiting activity, e.g. Cdk2 and especially Cdc7 inhibiting activity.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkeft's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of PKs, Cdk2 and Cdc7 in the regulation of cellular proliferation, these pyrimidylpyrroles are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

The compounds of the invention can be also active as inhibitors of other protein kinases such as, for instance, protein kinase C in different isoforms, Met, PAK4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, PI3K, weel kinase, Src, Abl, Akt, ILK, MK-2, IKK-2, Cdk in different isoforms, Nek, and thus be effective in the treatment of diseases associated with other protein kinases.

Accordingly, in a first embodiment, the present invention provides a method for treating cell proliferative disorders caused by and/or associated with an altered protein kinase activity by administering to a mammal in need thereof an effective amount of a pyrimidylpyrrole derivative represented by formula (I)

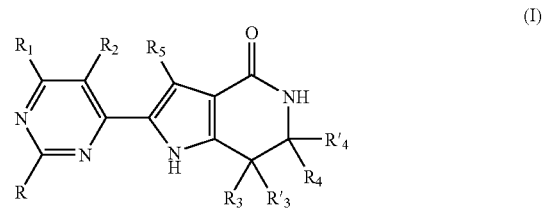

wherein

R is a hydrogen atom or a group selected from amino, arylamino, optionally substituted $C_1$-$C_6$ alkylamino, optionally substituted arylalkylamino, heteroarylalkylamino, $C_1$-$C_6$ dialkylamino and acylamino;

$R_1$ and $R_2$ are, each independently, a hydrogen or halogen atom, a straight or branched $C_1$-$C_6$ alkyl group, an amino or arylamino group or, taken together with the pyrimidine bond to which they are linked, $R_1$ and $R_2$ may form a divalent —NH—CH=N—, —N=CH—NH— or —NH—CH=CH— group;

$R_3$, $R'_3$, $R_4$ and $R'_4$ are, each independently, a hydrogen atom or a group selected from straight or branched $C_1$-$C_6$ alkyl, $C_3$-$C_6$ cycloalkyl, heterocyclyl, aryl, cycloalkyl-alkyl, heterocyclyl-alkyl or aryl-alkyl; or $R_3$ and $R_3$'or $R_4$ and $R_4$', taken together, form a $C_3$-$C_6$ cyclic alkyl group;

$R_5$ is a hydrogen or halogen atom or a straight or branched $C_1$-$C_6$ alkyl group and pharmaceutically acceptable salts thereof.

The above method enables treatment of cell proliferative disorders caused by and/or associated with an altered Cdc7 kinase activity.

In a preferred embodiment of the method described above, the cell proliferative disorder is cancer.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

The present invention also provides a pyrimidylpyrrole derivative which is represented by formula (I)

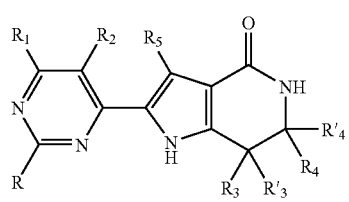

(I)

wherein

R is a hydrogen atom or a group selected from amino, arylamino, optionally substituted $C_1$-$C_6$ alkylamino, optionally substituted arylalkylamino, heteroarylalkylamino, $C_1$-$C_6$ dialkylamino and acylamino;

$R_1$ and $R_2$ are, each independently, a hydrogen or halogen atom, a straight or branched $C_1$-$C_6$ alkyl group, an amino or arylamino group or, taken together with the pyrimidine bond to which they are linked, $R_1$ and $R_2$ may form a divalent —NH—CH=N—, —N=CH—NH— or —NH—CH=CH— group;

$R_3$, $R'_3$, $R_4$ and $R'_4$ are, each independently, a hydrogen atom or a group selected from straight or branched $C_1$-$C_6$ alkyl, $C_3$-$C_6$ cycloalkyl, heterocyclyl, aryl, cycloalkyl-alkyl, heterocyclyl-alkyl or aryl-alkyl; or $R_3$ and $R_3'$ or $R_4$ and $R_4'$, taken together, form a $C_3$-$C_6$ cyclic alkyl group;

$R_5$ is a hydrogen or halogen atom or a straight or branched $C_1$-$C_6$ alkyl group and pharmaceutically acceptable salts thereof.

The present invention also includes methods of synthesizing the pyrimidylpyrrole derivatives of formula (I), and the pharmaceutical compositions comprising them. A more complete appreciation of the invention and many of the attendant advantages thereof will be readily obtained as the same becomes better understood by reference to the following detailed description.

DETAILED DESCRIPTION OF THE INVENTION

Several heterocyclic compounds are known in the art as protein kinase inhibitors. Among them are, for instance, pyrrolo-pyrazoles disclosed in WO 02/12242; tetrahydroindazoles disclosed in WO 00/69846; pyrrolo-pyridines disclosed in WO 01/98299; aminophthalazinones disclosed in WO 03/014090 and aminoindazoles disclosed in WO 03/028720.

In addition, pyridylpyrrole derivatives endowed with mitogen activated protein kinase-activated protein kinase-2 inhibitory activity are disclosed in the published PCT International Patent Application WO 04/058762 (published Jul. 15, 2004), claiming priority of U.S. Ser. No. 60/434,962, filed in Dec. 12, 2002.

Among the compounds therein disclosed are, in particular, pyridylpyrroles which are substituted by aryl- or arylalkenyl-groups at the pyridine moiety; pyridylpyrroles being substituted by amino groups or halogen atoms at this same pyridine ring are also therein disclosed as synthetic intermediates.

Interestingly, the compounds of the invention fall within the broad general formula disclosed in the aforementioned patent application U.S. 60/434,962 but are not specifically exemplified therein.

The compounds of formula (I) of the invention may have asymmetric carbon atoms and may therefore exist as individual optical isomers, as racemic admixtures or as any other admixture including a majority of one of the two optical isomers, which are all to be intended as comprised within the scope of the present invention.

Likewise, the use as an antitumor agent of all the possible isomers and their admixtures and of both the metabolites and the pharmaceutically acceptable bio-precursors (otherwise referred to as pro-drugs) of the compounds of formula (I) are also within the scope of the present invention.

Prodrugs are any covalently bonded compounds which release the active parent drug, according to formula (I), in vivo.

In cases when compounds may exist in tautomeric forms, for instance keto-enol tautomers, each tautomeric form is contemplated as being included within this invention whether existing in equilibrium or predominantly in one form.

In the present description, unless otherwise specified, with the term straight or branched $C_1$-$C_6$ alkyl we intend any of the groups such as, for instance, methyl, ethyl, n-propyl, isopropyl, n-butyl, isobutyl, tert-butyl, sec-butyl, n-pentyl, n-hexyl, and the like.

With the term amino we intend an —$NH_2$ group whilst the term arylamino comprises any group —NH-aryl, wherein aryl is as defined below.

With the term aryl we intend any carbocyclic or heterocyclic hydrocarbon with from 1 to 2 ring moieties, either fused or linked to each other by single bonds, wherein at least one of the rings is aromatic. If present, any aromatic heterocyclic hydrocarbon also referred to as heteroaryl group, comprises a 5 to 6 membered ring with from 1 to 3 heteroatoms selected among N, O or S.

Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like. With the term $C_3$-$C_6$ cycloalkyl we intend any group such as cyclopropyl, cyclobutyl, cyclopentyl and cyclohexyl.

With the term heterocyclyl we intend any 5 or 6 membered heterocyclic ring comprising from 1 to 3 heteroatoms selected among N, O or S. Clearly, if the said heterocycle or heterocyclyl group is an aromatic heterocycle, also referred to as heteroaryl, it is encompassed by the above definition given to aryl groups.

As such, besides the above aromatic heterocycles, the term heterocyclyl also encompasses saturated or partially unsaturated heterocycles such as, for instance, pyrroline, pyrrolidine, imidazoline, imidazolidine, pyrazoline, pyrazolidine, piperidine, piperazine, morpholine, and the like.

With the term acylamino we intend any of $C_1$-$C_6$ alkylcarbonylamino, $C_3$-$C_7$ cycloalkylcarbonylamino, cycloalkylalkylcarbonylamino group, any arylcarbonylamino, heteroarylcarbonylamino, arylalkylcarbonylamino and heteroarylalkylcarbonylamino group. From the above, it is clear to the skilled person that any group whose name is identified as a composite name such as, for instance, cycloalkyl-alkyl, heterocyclyl-alkyl, arylalkyl and the like, have all to be intended as construed by the moieties from which they derive. In this respect, as an example, any group which is identified as an arylalkyl has to be intended as an alkyl group which is further substituted by aryl, wherein both aryl and alkyl are as above defined.

Clearly when $R_3$ and $R_3'$ or $R_4$ and $R_4'$, taken together, form a $C_3$-$C_6$ cyclic alkyl group, the compound is referred to as spiro derivative.

When alkylamino or arylalkylamino group is optionally substituted, the substituents are chosen from alkyl, cycloalkyl, haloalkyl, amino, hydroxy, alkoxy, halogen, alkoxycarbonyl, aminocarbonyl and alkylcarbonylamino as herein defined.

Clearly, when $R_1$ and $R_2$ are linked together as forming any divalent group —NH—CH=N—, —N=CH—NH— or —NH—CH=CH—, purine and fused pyrimidine-pyrrole systems are obtained as having the following formulae, still being an object of the invention

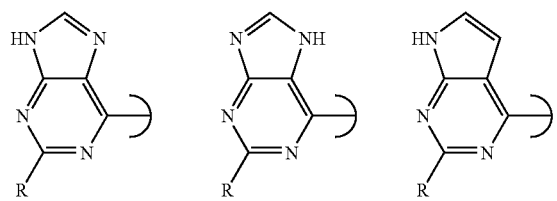

Pharmaceutically acceptable salts of the compounds of formula (I) include the acid addition salts with inorganic or organic acids such as, for instance, nitric, hydrochloric, hydrobromic, sulfuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid.

A preferred class of compounds of the invention is represented by the derivatives of formula (I) wherein R is hydrogen, amino or phenylamino; $R_1$ and $R_2$ are both hydrogen atoms or, taken together with the pyrimidine bond to which they are linked, form a divalent —NH—CH=N— group; and $R_3$, $R'_3$, $R_4$, $R'_4$ and $R_5$ are as above defined.

Another class of preferred compounds of the invention is represented by the derivatives of formula (I) wherein at least one of $R_3$ and $R'_3$ is a hydrogen atom.

Another class of preferred compounds of the invention is represented by the derivatives of formula (I) wherein at least one of $R_4$ and $R'_4$ is a hydrogen atom.

Still more preferred compounds of the invention are the derivatives of formula (I) wherein $R_1$, $R_2$ are both hydrogen atoms.

For a reference to any specific compound of formula (I) of the invention, optionally in the form of a pharmaceutically acceptable salt, see the experimental section and claims. As formerly indicated, a further object of the present invention is represented by the process for preparing the compounds of formula (I).

The compounds of formula (I) may be prepared according to the following synthetic scheme, by reacting the pyrimidine derivative of formula (III) with a suitable piperidine-dione derivative of formula (IV) wherein Q is H or a suitable nitrogen protecting group, preferably tert-butoxycarbonyl.

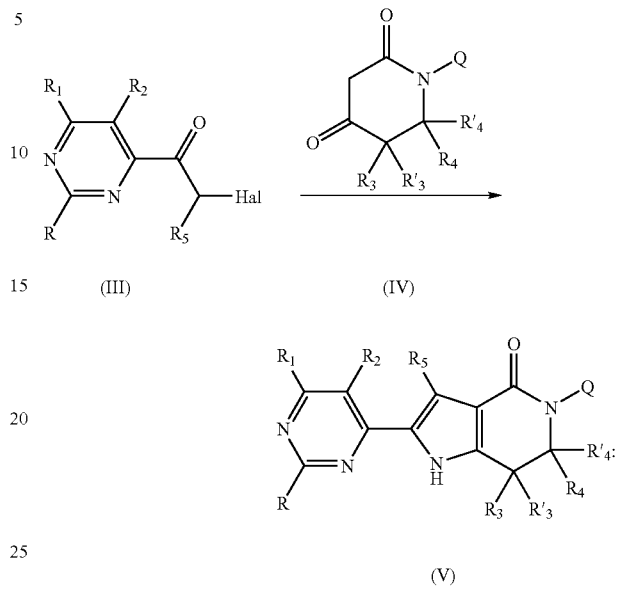

The reaction occurs in the presence of ammonium acetate and of a suitable solvent such as, for instance, a lower alcohol. Preferably, the reaction is carried out in the presence of ethanol by working at room temperature and for a suitable time varying from about 2 hours to about 24 hours. If necessary compound (V) is converted into compound (I) by removal of the protecting group Q.

Therefore, the compounds of formula (I) and the pharmaceutically acceptable salts thereof may be obtained by a process comprising:

a) halogenating a compound of formula (II) so as to obtain a compound of formula (III)

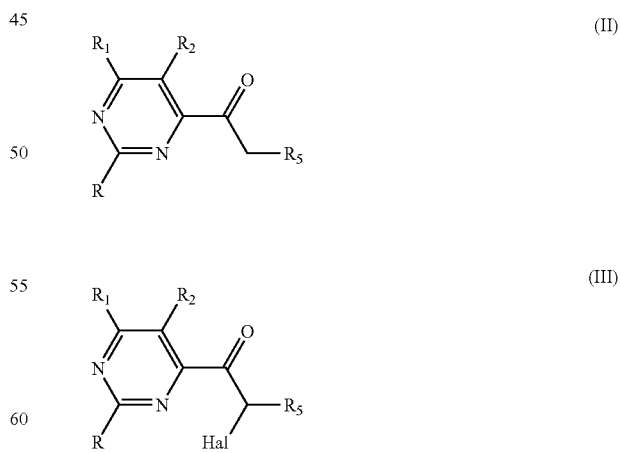

wherein R, $R_1$ and $R_2$ have the above reported meanings, $R_5$ is a hydrogen atom or a straight or branched $C_1$-$C_6$ alkyl group and Hal represents a suitable halogen atom, preferably bromine or chlorine;

b) reacting the compound of formula (III) with a compound of formula (IV)

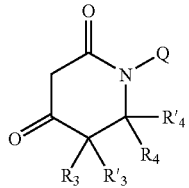

(IV)

wherein $R_3$, $R'_3$, $R_4$, $R'_4$ and Q have the above reported meanings, so as to obtain a compound of formula (I) and, optionally, converting it into another compound of formula (I) and/or into a pharmaceutically acceptable salt thereof.

The above process is an analogy process which can be carried out according to methods well known in the art.

According to step (a) of the process the compound of formula (II) is halogenated, in particular brominated or chlorinated, by working under conventional methods, for instance in the presence of bromine and in a suitable solvent such as acetic and hydrobromic acid mixtures, for a time varying from about 1 hour to about 24 hours. Alternatively, a suitable activated derivative of the compound of formula (II), for instance an enolether or silylether, can be reacted with a halogen source such as N-bromo-succinimide (NBS) in a suitable solvent such as, for instance, tetrahydrofuran/water mixtures, and the like.

According to step (b) of the process, the intermediate compound of formula (III) is then reacted with a compound of formula (IV), in the presence of ammonium acetate and of a suitable solvent such as, for instance, a lower alcohol. Preferably, the reaction is carried out in the presence of ethanol by working at room temperature and for a suitable time varying from about 2 hours to about 24 hours.

The final compound of formula (I) thus obtained may be then converted into another compound of formula (I) according to well-known methods in the art. As an example, the compounds of formula (I) wherein $R_5$ represents a hydrogen atom can be easily converted into the corresponding compounds of formula (I) wherein $R_5$ is a halogen atom, through conventional methods reported in the literature for the halogenation of pyrrole derivatives.

In another example, the compounds of formula (I), wherein R is an opt. substituted $C_1$-$C_6$ alkylamino or opt. substituted arylalkylamino or heteroarylalkylamino or $C_1$-$C_6$ dialkylamino can be obtained from another compound of formula (I) where R is amino by reductive amination.

Another example is represented by the preparation of compounds of formula (I), wherein R is an acylamino group by reacting a compound of formula (V), that is a protected form of a compound of formula (I), with a suitable acyl halide, as shown in the following scheme:

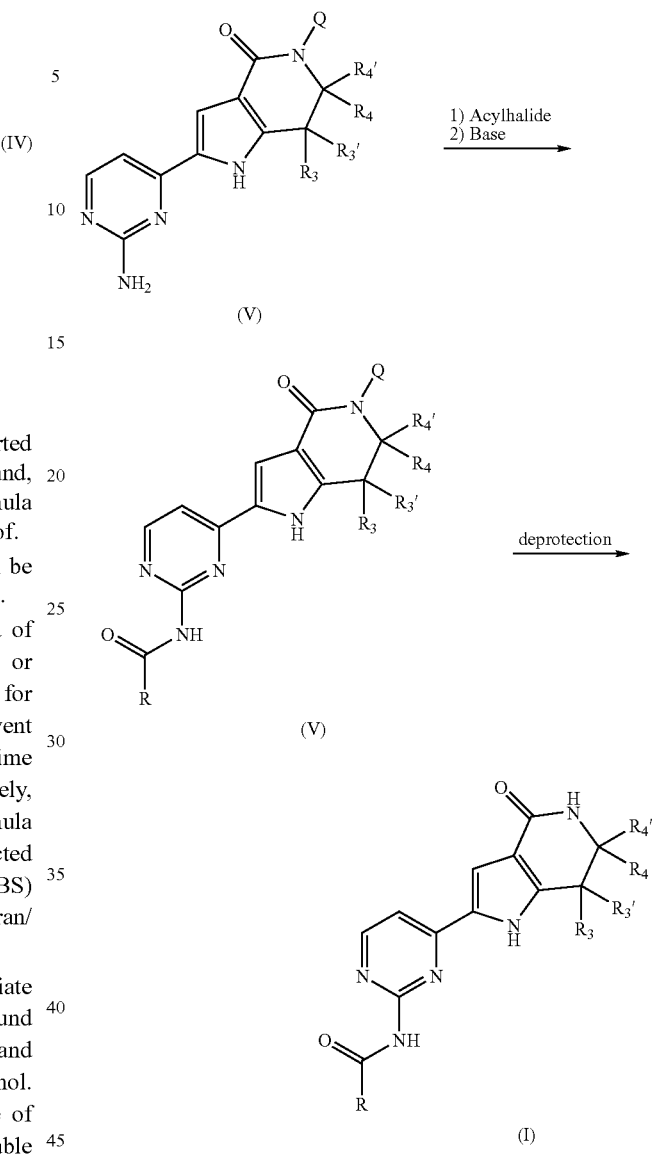

Likewise, the conversion of a compound of formula (I) into a pharmaceutically acceptable salt is easily carried out according to known methods, e.g. by contacting any free base of formula (I) with any suitable pharmaceutically acceptable acid.

The compounds of formula (II) and (IV), as well as any other reactant of the process, are known or they can be easily prepared according to known methods. As an example, the compounds of formula (II) wherein R is amino (—$NH_2$) or arylamino (—NH—Ar) may be obtained according to the following path:

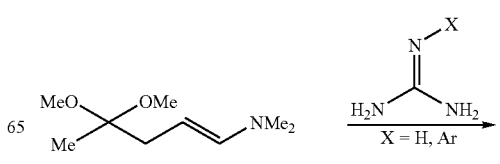

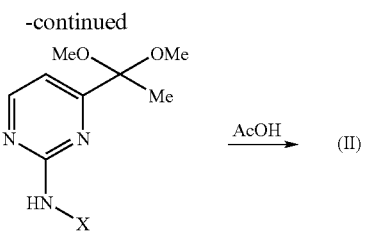

1-(Dimethylamino)-4,4-dimethoxy-1-penten-3-one is a known compound which can be prepared according to known methods, for instance as reported in J. Het. Chem., 22(6), 1723-6, 1985. It is easily reacted with guanidine or a guanidine derivative thereof, for instance being available in the form of an acid addition salt, e.g. as guanidinium hydrochloride salt. The reaction is carried out under basic conditions, for instance in the presence of sodium ethylate and of a suitable solvent such as a lower alcohol, preferably ethanol. The reaction occurs at refluxing temperature, for a suitable time up to about 24 hours.

In their turn, guanidine and derivatives thereof are known and if not commercially available per se can be easily prepared according to known methods.

The above reaction allows to obtain the intermediate pyrimidine compound which is then converted into the compound of formula (II) through acidic treatment at room temperature, for instance in the presence of acetic acid.

Likewise, the compounds of formula (II) wherein $R_1$ and $R_2$ are linked together through the divalent —N=CH—NH— group so as to form a purine system, may be obtained from commercially available 6-chloro-9H-purine. In this respect, the halogenated derivative of formula (III) may be directly obtained as per the synthetic scheme below, without the need of isolating the intermediate purine compound of formula (II):

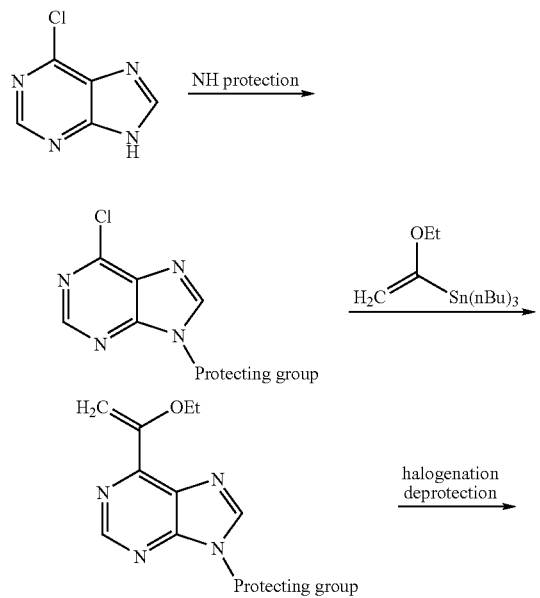

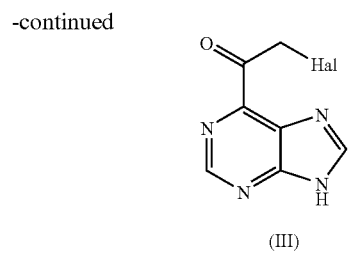

6-Chloro-9H-purine is thus protected at the imidazole nitrogen atom according to conventional methods, for instance with 3,4-dihydro-2H-pyran in the presence of p-toluenesulfonic acid, so as to get the corresponding 6-chloro-purine derivative wherein the protecting group is, e.g., tetrahydro-2H-pyran-2-yl.

This derivative is then reacted with 1-(ethoxyvinyl)tributyltin and in the presence of palladium tetrakis triphenylphosphine so as to obtain the corresponding 6-(1-ethoxyvinyl)purine derivative. This latter intermediate compound is then directly converted into the halogenated derivative of formula (III) with proper halogenating agents and in the presence of suitable solvents, as formerly reported.

By working in an analogous method and by using any proper starting material, additional compounds of formula (II), for instance those wherein $R_1$ and $R_2$ form a divalent —NH—CH=CH— group, may be thus obtained.

The compounds of formula (I) wherein one or both of $R_1$ and $R_2$ are other than hydrogen atoms are prepared according to the process object of the invention by starting from the corresponding pyrimidine derivatives of formula (II).

Also the piperidine-dione derivative (IV) is a known compound or, alternatively, can be prepared by known methods, for instance according to the synthetic pathway below, wherein Alk stands for a suitable lower alkyl group, e.g. ethyl, and A stands for chloro or OAlk:

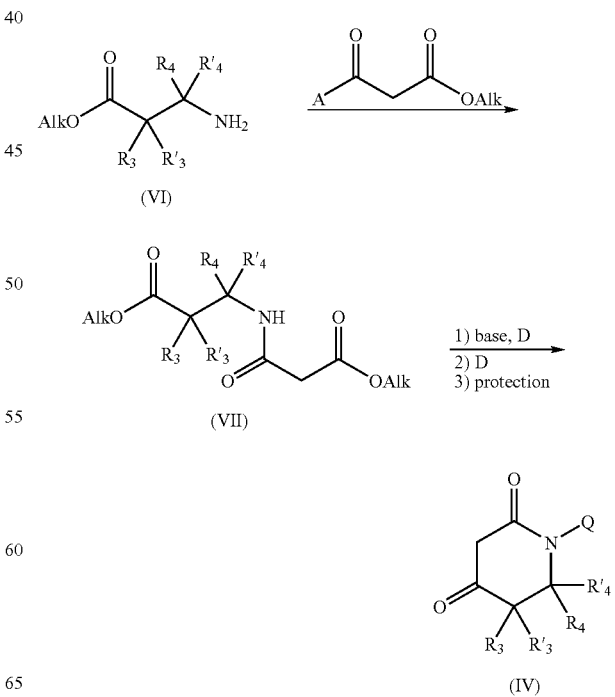

In this respect, a suitable β-amino-carboxyester (VI) derivative wherein $R_3$, $R'_3$, $R_4$ and $R'_4$ have the above reported meanings, is reacted with dialkylmalonate or, alternatively, with 3-chloro-3-oxopropanoic acid alkyl ester, for instance, dimethylmalonate or ethyl 3-chloro-3-oxopropanoate, respectively. When A is chloro the reaction is carried out under basic conditions, for instance in the presence of triethylamine, and in a suitable solvent such as dichloromethane, at a temperature comprised between room temperature to reflux. When A is OAlk the reaction is carried out with or without basic conditions and more conveniently in the absence of solvents at reflux temperature of the dialkylmalonate.

When not commercially available, the above mentioned β-amino-carboxyester derivatives (VI) can be obtained according to well known procedures described in the literature. The intermediate derivative thus obtained (VII) is then converted into the compound of formula (IV) in a two-steps reaction, by first reacting it under basic conditions, e.g. in the presence of sodium methylate and of a suitable solvent, preferably toluene, at refluxing temperature and for a time varying between about 2 hours and about 24 hours. Subsequently, the product of the former step is reacted as such, without being isolated, with an acetonitrile/water/acetic acid mixture under refluxing conditions and for a time varying between about 12 hours and about 24 hours. Optionally the piperidin-dione (IV) can be protected with a suitable protecting group Q.

In the alternative, the piperidine-dione derivative (IV) can be prepared, for instance, according also to the alternative synthetic pathway below:

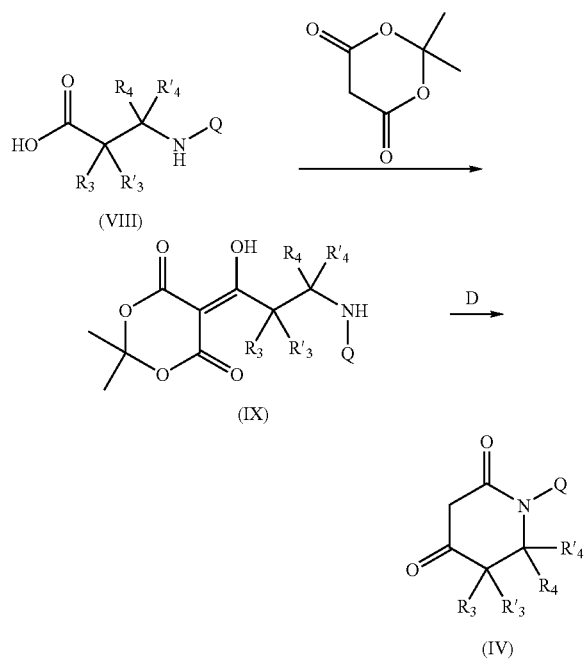

In the procedure, Meldrum's acid (2,2-dimethyl-1,3-dioxane-4,6-dione) is reacted with a suitable aminoacid derivative of formula (VIII) so as to obtain a compound of formula (IX) wherein Q is a suitable nitrogen protecting group and $R_3$, $R'_3$, $R_4$ and $R'_4$ are as above defined. The compound of formula (IX) is then cyclized by dissolving it in a suitable solvent, for instance ethylacetate, and refluxing for a period of time from 1 to 24 hours;

or, in the alternative, the piperidine-dione derivative (IV) can be modified according to the synthetic pathway below, wherein Q stands for a suitable nitrogen-protecting group such as, in particular, tert-butoxycarbonyl, or other groups, such as p-methoxybenzyl, p-methoxyethylbenzyl, p-methoxyphenyl:

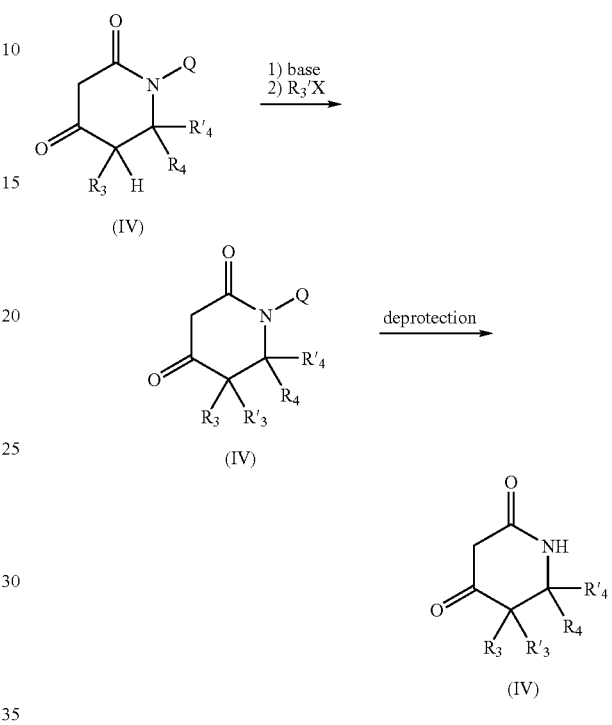

In this respect, a suitable piperidine-dione derivative (IV) wherein $R_3$, $R_4$ and $R'_4$ and Q have the above reported meanings, is reacted with a base, for instance lithium bis(trimethylsilyl)amide (LiHMDS). The reaction is carried out in a suitable solvent such as tetrahydrofuran, at a temperature comprised between −78° C. and room temperature.

The reaction mixture is then treated with a suitable alkyl halide thus obtaining another compound of formula (IV). The compound thus obtained, where Q is for instance a tert-butoxycarbonyl group, can be converted into another compound of formula (IV) by treating it with acidic conditions, e.g. in the presence of trifluoroacetic acid and of a suitable solvent, preferably dichloromethane, at room temperature and for a time comprised between about 1 hours and about 6 hours.

From all of the above, it is clear to the skilled person that when preparing the compounds of formula (I) according to the aforementioned process, comprehensive of any variant thereof, optional functional groups within the starting materials or the intermediates thereof and which could give rise to unwanted side reactions, need to be properly protected according to conventional techniques. Likewise, the conversion of these latter into the free deprotected compounds may be carried out according to known procedures.

By analogy, any compound of formula (I) which is susceptible of being salified can be easily converted into the corresponding acid addition salt, by working in the presence of any pharmaceutically acceptable acid, for instance selected among those previously reported. As it will be readily appreciated, if the compounds of formula (I) prepared according to the process described above are obtained as a mixture of isomers, their separation into the single isomers of formula (I), according to conventional techniques, is also within the scope of the present invention. Conventional techniques for racemate resolution include, for instance, partitioned crystallization of diastereoisomeric salt derivatives or preparative chiral HPLC.

Pharmacology

The compounds of formula (I) are active as protein kinase inhibitors and are therefore useful, for instance, to restrict the unregulated proliferation of tumor cells.

In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative Cdc7 inhibitors and the potency of selected compounds is determined through a method of assay based on the use of Dowex resin capture technology. The assay consists of the transfer of radioactivity labeled phosphate moiety by the kinase to an acceptor substrate. The resulting 33P-labeled product is separated from unreacted tracer, transferred into a scintillation cocktail and light emitted is measured in a scintillation counter.

Inhibition Assay of Cdc7/Dbf4 Activity

The inhibition assay of Cdc7/Dbf4 activity is performed according to the following protocol. The MCM2 substrate is trans-phosphorylated by the Cdc7/Dbf4 complex in the presence of ATP traced with $\gamma^{33}$-ATP. The reaction is stopped by addition of Dowex resin in the presence of formic acid. Dowex resin particles capture unreacted $\gamma^{33}$-ATP and drag it to the bottom of the well while $^{33}P$ phosphorylated MCM2 substrate remains in solution. The supernatant is collected, transferred into Optiplate plates and the extent of substrate phosphorylation is evaluated by β counting.

The inhibition assay of Cdc7/Dbf4 activity was performed in 96 wells plate according to the following protocol.

To each well of the plate were added:

10 μl test compound (10 increasing concentrations in the nM to μM range to generate a dose-response curve). The solvent for test compounds contained 3% DMSO. (final concentration 1%)

10 μl substrate MCM2 (6 μM final concentration), a mixture of cold ATP (2 μM final concentration) and radioactive ATP (1/5000 molar ratio with cold ATP).

10 μl enzyme (Cdc7/Dbf4, 2 nM final concentration) that started the reaction. The buffer of the reaction consisted in 50 mM HEPES pH 7.9 containing 15 mM $MgCl_2$, 2 mM DTT, 3 μM $NaVO_3$, 2 mM glycerophosphate and 0.2 mg/ml BSA.

After incubation for 60 minutes at room temperature, the reaction was stopped by adding to each well 150 μl of Dowex resin in the presence of 150 mM formic acid. After another 60 min incubation, 50 μL of suspension were withdrawn and transferred into 96-well OPTIPLATEs containing 150 μl of MicroScint 40 (Packard); after 5-10 minutes shaking the plates were read for 1 min in a Packard TOP-Count radioactivity reader.

IC50 determination: inhibitors were tested at different concentrations ranging from 0.0005 to 10 μM. Experimental data were analyzed by the computer program Assay Explorer using the four parameter logistic equation:

$$y=\text{bottom}+(\text{top}-\text{bottom})/(1+10^{((\log IC50-x)*\text{slope})})$$

where x is the logarithm of the inhibitor concentration, y is the response; y starts at bottom and goes to top with a sigmoid shape.

The inhibiting activity of putative cdk/cyclin inhibitors and the potency of selected compounds may be determined through a method of assay based on the use of the SPA technology (Amersham Pharmacia Biotech).

The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay of cdk2/Cyclin A Activity

Kinase reaction: 4 μM in house biotinylated histone H1 (Sigma # H-5505) substrate, 10 μM ATP (0.1 microCi $P^{33}\gamma$-ATP), 1.1 nM Cyclin A/CDK2 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 60 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: inhibitors were tested at different concentrations ranging from 0.0015 to 10 μM. Experimental data were analyzed by the computer program GraphPad Prizm using the four parameter logistic equation:

$$y=\text{bottom}+(\text{top}-\text{bottom})/(1+10^{((\log IC50-x)*\text{slope})})$$

where x is the logarithm of the inhibitor concentration, y is the response; y starts at bottom and goes to top with a sigmoid shape.

Ki calculation:

Experimental method: Reaction was carried out in buffer (10 mM Tris, pH 7.5, 10 mM $MgCl_2$, 0.2 mg/ml BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates were read on a top counter. Control (time zero) for each ATP and histone concentrations was measured.

Experimental design: Reaction velocities are measured at four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allows the selection of a single endpoint time (10 min) in the linear range of the reaction for the Ki determination experiment.

Kinetic parameter estimates: Kinetic parameters were estimated by simultaneous nonlinear least-square regression using [Eq.1] (competitive inhibitor respect to ATP, random mechanism) using the complete data set (80 points):

$$v = \frac{Vm \circ A \circ B}{\alpha \circ Ka \circ Kb + \alpha \circ Ka \circ B + a \circ Kb \circ A + A \circ B + \alpha \circ \frac{Ka}{Ki} \circ I \circ \left(Kb + \frac{B}{\beta}\right)}$$ [Eq. 1]

where A=[ATP], B=[Substrate], I=[inhibitor], Vm=maximum velocity, Ka, Kb, Ki the dissociation constants of ATP, substrate and inhibitor respectively. α and β the cooperativity factor between substrate and ATP binding and substrate and inhibitor binding respectively.

As an example, some representative compounds of the invention were tested as formerly reported against Cdc7/Dbf4 and Cdk2, showing an inhibitory activity, expressed as IC50 (nM), as follows:

2-(2-aminopyrimidin-4-yl)-1,5,6,7-tetrahydro-4H-pyrrolo[3,2-c]pyridin-4-one hydrochloride IC50 Cdc7: 11 nM;

2-(2-aminopyrimidin-4-yl)-7-phenyl-1,5,6,7-tetrahydro-4H-pyrrolo[3,2-c]pyridin-4-one hydrochloride IC50 Cdc7: 15 nM;

2-(2-phenylaminopyrimidin-4-yl)-1,5,6,7-tetrahydro-4H-pyrrolo[3,2-c]pyridin-4-one hydrochloride IC50 Cdc7: 7 nM;

2-(9H-purin-6-yl)-1,5,6,7-tetrahydro-4H-pyrrolo[3,2-c]pyridin-4-one hydrochloride IC50 Cdc7: 200 nM;

2-pyrimidin-4-yl-1,5,6,7-tetrahydro-4H-pyrrolo[3,2-c]pyridin-4-one hydrochloride IC50 Cdc7: 19 nM;

7-phenyl-2-(9H-purin-6-yl)-1,5,6,7-tetrahydro-4H-pyrrolo[3,2-c]pyridin-4-one hydrochloride IC50 Cdc7: 90 nM;

2-(2-aminopyrimidin-4-yl)-6,6-dimethyl-1,5,6,7-tetrahydro-4H-pyrrolo[3,2-c]pyridin -4-one hydrochloride IC50 Cdc7: 32 nM;

7-phenyl-2-pyrimidin-4-yl-1,5,6,7-tetrahydro-4H-pyrrolo[3,2-c]pyridin-4-one hydrochloride IC50 Cdc7: 32 nM;

2-(2-anilinopyrimidin-4-yl)-7-phenyl-1,5,6,7-tetrahydro-4H-pyrrolo[3,2-c]pyridin-4-one hydrochloride IC50 Cdc7: 29 nM;

2-(2-aminopyrimidin-4-yl)-6-isopropyl-1,5,6,7-tetrahydro-4H-pyrrolo[3,2-c]pyridin-4-one IC50 Cdc7: 9 nM;

2-(2-aminopyrimidin-4-yl)-7-methyl-1,5,6,7-tetrahydro-4H-pyrrolo[3,2-c]pyridin-4-one IC50 Cdc7: 8 nM;

2-(2-aminopyrimidin-4-yl)-6-methyl-1,5,6,7-tetrahydro-4H-pyrrolo[3,2-c]pyridin-4-one IC50 Cdc7: 26 nM;

2-(2-aminopyrimidin-4-yl)-7,7-dimethyl-1,5,6,7-tetrahydro-4H-pyrrolo[3,2-c]pyridin-4-one IC50 Cdc7: 2 nM;

2-(2-aminopyrimidin-4-yl)-6-isobutyl-1,5,6,7-tetrahydro-4H-pyrrolo[3,2-c]pyridin-4-one IC50 Cdc7: 4 nM;

ethyl 4-(4-oxo-4,5,6,7-tetrahydro-1H-pyrrolo[3,2-c]pyridin-2-yl)pyrimidin-2-ylcarbamate IC50 Cdc7: 80 nM;

(7R or 7S)-2-(2-aminopyrimidin-4-yl)-7-methyl-1,5,6,7-tetrahydro-4H-pyrrolo[3,2-c]pyridin-4-one IC50 Cdc7: 5 nM;

(7R or 7S)-2-(2-aminopyrimidin-4-yl)-7-methyl-1,5,6,7-tetrahydro-4H-pyrrolo[3,2-c]pyridin-4-on IC50 Cdc7: 4 nM;

2-(2-aminopyrimidin-4-yl)-3-iodo-1,5,6,7-tetrahydro-4H-pyrrolo[3,2-c]pyridin-4-one IC50 Cdc7: 4 nM;

2-(2-aminopyrimidin-4-yl)-7,7-diethyl-1,5,6,7-tetrahydro-4H-pyrrolo[3,2-c]pyridin-4-one IC50 Cdc7: 7 nM;

2-{2-[(2-furylmethyl)amino]pyrimidin-4-yl}-1,5,6,7-tetrahydro-4H-pyrrolo[3,2-c]pyridin-4-one IC50 Cdc7: 74 nM;

N-[4-(4-oxo-4,5,6,7-tetrahydro-1H-pyrrolo[3,2-c]pyridin-2-yl)pyrimidin-2-yl]benzamide IC50 Cdc7: 300 nM;

2-(2-aminopyrimidin-4-yl)-7-isopropyl-1,5,6,7-tetrahydro-4H-pyrrolo[3,2-c]pyridin-4-one IC50 Cdc7: 8 nM;

2-[2-(benzylamino)pyrimidin-4-yl]-1,5,6,7-tetrahydro-4H-pyrrolo[3,2-c]pyridin-4-one IC50 Cdc7: 270 nM;

2-[2-(propylamino)pyrimidin-4-yl]-1,5,6,7-tetrahydro4H-pyrrolo[3,2-c]pyridin-4-one IC50 Cdc7: 310 nM; IC50 Cdk2: 35 nM;

2-[2-(isobutylamino)pyrimidin-4-yl]-1,5,6,7-tetrahydro-4H-pyrrolo[3,2-c]pyridin-4-one IC50 Cdk2: 50 nM;

2-{2-[(cyclohexylmethyl)amino]pyrimidin-4-yl}-1,5,6,7-tetrahydro-4H-pyrrolo[3,2-c]pyridin-4-one IC50 Cdc7: 680 nM; IC50 Cdk2: 220 nM;

2-{2-[(2-furylmethyl)amino]pyrimidin-4-yl}-1,5,6,7-tetrahydro-4H-pyrrolo[3,2-c]pyridin-4-one IC50 Cdc7: 87 nM; IC50 Cdk2: 80 nM and N-[4-({[4-(4-oxo-4,5,6,7-tetrahydro-1H-pyrrolo[3,2-c]pyridin-2-yl)pyrimidin-2-yl]amino}methyl)phenyl]acetamide trifluoroacetate IC50 Cdc7: 300 nM; IC50 Cdk2: 20 nM.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route. For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

General Methods

Flash Chromatography was performed on silica gel (Merck grade 9395, 60A). HPLC was performed on Waters X Terra RP 18 (4,6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 minutes. UV detection at 220 nm and 254 nm. Flow rate 1 ml/min. Injection volume 10 μl. Full scan, mass range from 100 to 800 amu. Capillary voltage was 2.5 KV; source temp. was 120° C.; cone was 10 V. Retention times (HPLC r.t.) are given in minutes at 220 nm or at 254 nm. Mass are given as m/z ratio.

When necessary, compounds have been purified by preparative HPLC on a Waters Symmetry C18 (19×50 mm, 5 um) column using a Waters preparative HPLC 600 equipped with a 996 Waters PDA detector and a Micromass mod. ZMD single quadrupole mass spectrometer, electron spray ionization, positive mode. Mobile phase A was water 0.01% TFA, and Mobile phase B was acetonitrile. Gradient from 10 to 90% B in 8 min, hold 90% B 2 min. Flow rate 20 ml/min.

1H-NMR spectrometry was performed on a Mercury VX 400 operating at 400.45 MHz equipped with a 5 mm double resonance probe [1H (15N-31P) ID_PFG Varian].

The compounds of formula (I), having an asymmetric carbon atom and obtained as racemic mixture, were resolved by HPLC separation on chiral columns. In particular, for example, preparative columns CHIRALPACK® AD, CHIRALPACK® AS, CHIRALCELL® OJ can be used.

EXAMPLE 1

2-bromo-1-pyrimidin-4-ylethanone hydrobromide

The title compound was prepared by working as described in J. Med. Chem. 1992, 35, 3288. Onto a stirred solution of pyrimidine (2.5 g, 31.2 mmols) and acetaldehyde (10.8 mL, 192 mmols) in dichloromethane (190 mL) at about 0° C., 3.4 M sulphuric acid (15.6 mL) was added dropwise. The solution was cooled to −5° C. and, from two distinct dropping funnels, two solutions were simultaneously dropped therein in about 30 minutes: an 80% solution of tert-butylhydroperoxide in di-tert-butylperoxide/water (23.4 mL) and a solution of ferrous sulphate heptahydrate (52.2 g) in 100 mL of water. After addition, the reaction mixture was stirred at 0° C. for 2.5 hours, then the phases were separated and the aqueous phase was extracted with dichloromethane (2×150 mL). The joined organic phases were washed with a 10% aqueous sodium iodide solution, with $Na_2S_2O_5$ (10% aqueous solution) and with brine and then were dried over $Na_2SO_4$. Upon concentration, the obtained yellow solid was taken up with petroleum ether and filtered. After drying, the title compound was obtained as a brownish solid (0.87 g, Y=23%).

$^1$H NMR (DMSO-$d_6$/300 MHz) δ ppm 5.0 (s, 2H), 7.98 (d, 1H), 9.12 (d, 1H), 9.42 (s, 1H). bs, 1H).

EXAMPLE 2

1-(2-aminopyrimidin-4-yl)-2-bromoethanone hydrobromide

The title compound (a) was prepared by working as described in J. Het. Chem. 1985, 22, 1723.

A mixture of 3,3-dimethoxy-2-butanone (25 g, 189.16 mmol) and N,N-dimethylformamide dimethylacetal (22.5 g, 189.16 mmol) were stirred at 110° C. for 30 hours and then distilled (115° C., 1 mmHg) thus obtaining 1-(dimethylamino)-4,4-dimethoxypent-1-en-3-one, as a yellow solid (27.3 g, 146 mmol, 77%).

Onto a solution of sodium (3.48 g, 151.67 mmol) in anhydrous ethanol (400 mL), solid guanidine hydrochloride (14.5 g, 151.67 mmol) was added at r.t., to give a white suspension into which a solution of 1-(dimethylamino)-4,4-dimethoxypent-1-en-3-one (28.4 g, 151.67 mmol) in anhydrous ethanol (50 mL) was added. The mixture was refluxed for 19 hours. After cooling, the precipitate was filtered and washed with ethanol and with plenty of water, thus obtaining a white solid (8.56 g). The ethanolic solutions were concentrated to dryness, taken up with boiling ethyl acetate (1000 mL), filtered while hot and then cooled to yield a second crop. Total amount of 4-(1,1-dimethoxyethyl)pyrimidin-2-amine: 17.66 g, 63.5%. A solution of the said amine (17.5 g, 95.5 mmol) in formic acid was stirred at r.t. for 6 hours and concentrated to dryness and the residue was stirred in ethanol (50 mL) and then filtered thus obtaining 1-(2-aminopyrimidin-4-yl)ethanone (9.2 g, 70%). To a solution of 1-(2-aminopyrimidin-4-yl)ethanone (412 mg, 3 mmol) in glacial acetic acid (1 mL) and 48% aq. HBr (0.3 mL), bromine (0.153 mL) in acetic acid (0.4 mL) was added and the resulting orange solution was stirred at r.t. for 15 hours. After diluting with ethyl acetate (15 mL) the precipitate was filtered and washed with ethyl acetate thus affording the title compound as a whitish solid (580 mg, 65%).

¹H NMR (DMSO-d$_6$/300 MHz) δ ppm: 4.9 (s, 2H), 7.0 (d, 2H), 8.5 (d, 2H). s, 6H), 2.49 (bs, 2H), 3.13 (bs, 2H), 8.13 (bs, 1H).

EXAMPLE 3

2-bromo-1-(9H-purin-6-yl)ethanone

A solution of 6-(1-ethoxyvinyl)-9-tetrahydro-2H-pyran-2-yl-9H-purine (430 mg, 1.57 mmols), being prepared as described in Tetrahedron, 53 (6), 2291-2302, (1997), in tetrahydrofuran (24 ml) and water (1.5 ml) was treated with N-bromo-succinimide (NBS, 280 mg, 1.57 mmols) and kept at room temperature for 15 minutes. The solution was evaporated under reduced pressure, taken up with water and filtered to obtain the title compound (312 mg, Y=82%) as a yellow solid.

¹H NMR (DMSO-d$_6$/300 MHz) δ ppm 5.12 (s, 2H), 8.85 (s, 1H), 9.14 (s, 1H)

EXAMPLE 4

1-(2-phenylaminopyrimidin-4-yl)-2-chloroethanone

To a solution of sodium (614 mg, 26.7 mmol) in anhydrous ethanol (70 mL), phenylguanidine (4.43 g, 13.35 mmol) was added followed by a solution of 1-(dimethylamino)-4,4-dimethoxypent-1-en-3-one (5 g, 26.7 mmol), obtained as previously described, in anhydrous ethanol (20 mL). The suspension was refluxed for 20 hours, then ⅔ of the solvent were removed and water (250 mL) was added. The precipitate was extracted with ethyl acetate and the organic phase was washed with a sodium dihydrogenphosphate solution, with brine, dried over sodium sulphate and concentrated to yield the desired ketal (4.3 g). The ketal (4.2 g, 16.19 mmol) was dissolved in 88% formic acid (25 mL) and stirred at r.t. for 2.5 hours. The reaction mixture was diluted with water (200 mL), the precipitate was filtered and washed with abundant water. 1-(2-Phenylaminopyrimidin-4-yl)-ethanone was thus isolated as a yellow solid (3.1 g).

This ketone (1.3 g, 6.1 mmol) was dissolved in dichloromethane (40 mL), then TEA (5.1 mL, 36.6 mmol) and tert-butyl-dimethyl-trifluoro methansulphonate (4.2 mL, 18.3 mmol) were added. The orange solution was stirred overnight, then diluted with more dichloromethane (150 mL), washed twice with a 5% sodium hydrogencarbonate solution (50 mL), with water, with brine, then dried over sodium sulphate and concentrated to give the bis-silylated derivative (2.67 g). To half of the material (1.32 g, 2.94 mmol) dissolved in tetrahydrofuran (THF, 25 mL) and cooled to 0° C., a solution of NBS (0.549 g, 3.09 mmol) in THF (10 mL) was added dropwise in 5 minutes. The reaction mixture was stirred at 0° C. for 1 hour, then 2 N HCl was added and the reaction mixture was stirred for 24 hours at r.t. The crude was purified by flash chromatography (eluant: hexane/ethyl acetate 5:1) to yield 0.325 g of title compound.

¹H NMR (DMSO-d$_6$/300 MHz) δ ppm: 4.9 (s, 2H), 6.7 (m, 1H), 6.9 (d, 1H), 7.0 (m, 2H), 7.4 (d, 2H), 8.4 (d, 1H), 9.6 (s, 1H).

EXAMPLE 5

Preparation of 6,6-dimethyl-2,4-dioxopiperidine

A solution of ethyl 3-methylbut-2-enoate (1 g, 7.8 mmol) in anhydrous ethanol (12 mL) was cooled to −20° C. and saturated with gaseous ammonia. The tube was sealed and kept at 90° C. for 24 hours. The reaction was cooled to room temperature, bubbled with nitrogen to eliminate the residual ammonia and treated with a 4 N solution of HCl in dioxane (1.9 mL). After 30 minute stirring, the mixture was evaporated under reduced pressure to give ethyl 3-amino-3-methylbutanoate hydrochloride as a grey solid (1.19 g, Y=84%).

¹H NMR (CDCl$_3$/400 MHz) δ ppm 1.2 (t, 3H), 1.26 (s, 6H), 2.65 (s, 2H), 4.1 (q, 2H), 8.27 (bs, 3H).

Ethyl 3-amino-3-methylbutanoate hydrochloride (0.87 g, 4.79 mmol) was suspended on methylene chloride (12 mL) and triethylamine (1.4 mL, 2.1 eq.). The mixture was cooled to 0° C. and treated dropwise with ethyl 3-chloro-3-oxopropanoate (0.64 mL, 1.05 eq.). The reaction was kept at room temperature for 2 hours, diluted with methylene chloride, washed with 1 N HCl and then with 5% NaHCO$_3$, dried over Na$_2$SO$_4$ and evaporated to dryness to obtain ethyl 3-[(3-ethoxy-3-oxopropanoyl)amino]-3-methylbutanoate (1.2 g, Y=97%) as a red oil.

¹H NMR (DMSO-d$_6$/300 MHz) δ ppm 1.11-1.21 (m, 6H), 1.29 (s, 6H), 2.71 (s, 2H), 3.14 (s, 2H), 3.95-4.15 (m, 4H), 7.75 (bs, 1H).

To a solution of sodium ethoxide, obtained from sodium metal (0.122 g, 5.55 mmol) in anhydrous ethanol (7 mL), a solution of ethyl 3-[(3-ethoxy-3-oxopropanoyl)amino]-3-methylbutanoate (1.2 g, 4.62 mmol) in dry toluene (7 mL) was added dropwise at room temperature, under stirring. The reaction mixture was heated at 80° C. for 2 hours then it was concentrated to reduced volume and the residue was dissolved in toluene (15 mL). The organic phase was extracted with water (40 mL), the aqueous phase was acidified to pH 2-3 with 1 N HCl and extracted with ethyl acetate (4×50 mL). The organic phase was washed with brine, dried over anhydrous sodium sulphate and concentrated to give ethyl 6,6-dimethyl-2,4-dioxopiperidine-3-carboxylate as a yellow solid (0.7 g, Y=71%) which was used for the next step without further purification.

Ethyl 6,6-dimethyl-2,4-dioxopiperidine-3-carboxylate (0.69 g, 3.23 mmol) was dissolved in acetonitrile containing 1% of water (15 mL) and the resulting solution was refluxed for 2 hours. After evaporating to dryness, the crude material was suspended in isopropyl ether, kept under vigorous stirring and filtered to give the title compound (387 mg, Y=85%) as a light brown solid.

¹H NMR (DMSO-d$_6$/300 MHz) δ ppm 1.18 (s, 6H), 2.49 (bs, 2H), 3.13 (bs, 2H), 8.13 (bs, 1H).

EXAMPLE 6

Preparation of 5-phenylpiperidine-2,4-dione

Ethyl cyano(phenyl)acetate (14.9 g, 78.83 mmol) was dissolved in absolute ethanol (400 mL) containing 37% hydrochloric acid (40 mL). The solution was treated with 10% Pd-C (2 g) and kept under hydrogen (40 psi) in a Parr apparatus for 24 hours. The resulting mixture was filtered to remove the catalyst and evaporated to dryness under reduced pressure. The residue was taken up with ethyl acetate, kept under vigorous stirring for 15 minutes and filtered. Obtained ethyl 3-amino-2-phenylpropanoate hydrochloride (11 g, Y=60%).

¹H NMR (DMSO-d₆/300 MHz) δ ppm 1.11 (t, 3H), 3.05 (dd, 1H, J=12.9, 6.15), 3.42 (dd, 1H, J=12.9, 8.79), 4.07 (m, 3H), 7.35 (m, 5H), 8.15 (br, 3H)

Ethyl 3-amino-2-phenylpropanoate hydrochloride (4.38 g, 19.13 mmol) was suspended in methylene chloride (80 mL) and triethylamine (5.86 mL, 2.2 eq.). The mixture was cooled to 0° C. and treated dropwise with ethyl 3-chloro-3-oxopropanoate (2.69 mL, 1.1 eq.). The reaction was kept at room temperature for one hour, diluted with methylene chloride, washed with 1 N HCl and then with 5% NaHCO₃, dried over Na₂SO₄ and evaporated to dryness. The crude material was chromatographed on silica gel, eluting with hexane/ethyl acetate 1/1, to give 3-(2-ethoxycarbonyl-acetylamino)-2-phenyl-propionic acid ethyl ester (4.24 g, Y=72%) as an oil.

¹H NMR (CDCl₃/300 MHz) δ ppm 1.21 (t, 3H), 1.27 (t, 3H), 3.26 (s, 2H), 3.73 (m, 2H), 3.89 (dd, 1H, J=6.16, 8.50), 4.17 (m, 4H), 7.29 (m, 6H).

Sodium (380 mg, 16.52 mmol) was dissolved in anhydrous ethanol (13 mL) and the resulting solution was treated dropwise with 3-(2-ethoxycarbonyl-acetylamino)-2-phenyl-propionic acid ethyl ester (4.23 g, 13.76 mmol) dissolved in anhydrous toluene (35 mL). The reaction was kept at 80° C. for 1.5 hours. After cooling, the mixture was extracted with water. The aqueous extracts were acidified with 2 N HCl, extracted with ethyl acetate and the organic layers were collected, dried over Na₂SO₄ and evaporated to dryness to obtain ethyl 2,4-dioxo-5-phenylpiperidine-3-carboxylate (1.73 g, Y=48%) which was used for the next step without further purification. Ethyl 2,4-dioxo-5-phenylpiperidine-3-carboxylate (1.73 g, 6.63 mmol) was dissolved in acetonitrile containing 1% of water (30 mL) and the resulting solution was refluxed for 2 hours. After evaporating to dryness, the crude material was chromatographed on silica gel, eluting with methylene chloride/methanol 92/8, to give the title compound (780 mg, Y=62%) as a solid.

¹H NMR (DMSO-d₆/300 MHz) δ ppm 3.25 (d, 1H, J=18.75) 3.42-3.70 (m, 2H), 3.61 (d, 1H, J=18.75), 3.81 (dd, 1H, J=5.57, 9.67), 7.26 (m, 5H), 8.20 (bs, 1H).

EXAMPLE 7

Preparation of ethyl 2-(aminomethyl)-3-methylbutanoate hydrochloride

Ethyl 2-cyano-3-methylbut-2-enoate (5.0 g, 32.6 mmol) was dissolved in 320 mL of absolute EtOH. 700 mg of PtO₂ and 12 mL of 4M HCl were added. The reaction mixture was hydrogenated at room temperature for 5 hours (30 psi). Filtration on a celite pad and evaporation of the solvent afforded crude title compound (quantitative yield).

1H NMR (400 MHz, DMSO-D6) δ ppm 0.90 (d, J=6.83 Hz, 3H) 0.93 (d, J=6.83 Hz, 3H) 1.24 (t, J=7.13 Hz, 3H) 1.92-2.06 (m, 1H) 2.53-2.60 (m, 1H) 2.84-3.17 (m, 2H) 4.05-4.24 (m, 2H) 7.84 (s, 3H) ESI (+) MS: m/z 160 (MH+).

By working in an analogous way and by starting from the suitable cyano derivative, the following compounds were also prepared:

ethyl 2-(aminomethyl)-3-methylpentanoate hydrochloride

¹H NMR (DMSO-d₆/400 MHz) δ ppm 0.80 (m, 6H) 1.23-1.40 (2 m, 5H) 1.76 (m, 1H) 2.69 (m, 1H) 2.89 (m, 1H), 3.09 (m, 1H) 4.14 (m, 2H) 7.82 (s, 3H) ESI (+) MS: m/z 174 (MH+).

ethyl 1-(aminomethyl)cyclopropanecarboxylate hydrochloride ESI (+) MS: m/z 144 (MH+).

EXAMPLE 8

Preparation of ethyl 2-{[(3-ethoxy-3-oxopropanoyl)amino]methyl}-3-methylbutanoate Crude ethyl 2-(aminomethyl)-3-methylbutanoate hydrochloride was dissolved in 200 mL of dry DCM and DIPEA was added (14 mL, 2.5 eq). After cooling to 0° C., ethyl 3-chloro-3-oxopropanoate was added (6.3 mL, 35.4 mmol). After stirring at room temperature overnight, the reaction mixture was diluted with DCM and washed with aq. KHSO₄ 5% (×2), aq. NaHCO₃ sat. sol. (×2) and brine. The organic layer was dried over Na₂SO₄, filtered and evaporated to dryness. Column chromatography (hexane/EtOAc=7/3→1/1) afforded 8.35 g (30.55 mmol, 93.4% yield) of target product.

1H NMR (400 MHz, DMSO-D6) δ ppm 0.89 (d, J=6.82 Hz, 3H) 0.93 (d, J=6.83 Hz, 3H) 1.20 (m, 6H) 1.82-1.90 (m, 1H) 2.35 (m, 1H) 3.19-3.33 (2 m, 4H) 4.06 (m, 4H) 8.11 (t, J=5.12 Hz, 1H) ESI (+) MS: m/z 274 (MH+).

By working in an analogous way and by starting from the suitable hydrochloride derivative, the following compounds were prepared:

ethyl 2-{[(3-ethoxy-3-oxopropanoyl)amino]methyl}-3-methylpentanoate

¹H NMR (DMSO-d₆/400 MHz) δ ppm 0.90 (m, 6H) 1.19-1.65 (3 m, 9H) 2.47 (m, 1H) 3.20 (m, 4H), 4.08 (m, 4H), 8.09 (m, 1H) ESI (+) MS: m/z 288 (MH+).

ethyl 1-{[(3-ethoxy-3-oxopropanoyl)amino]methyl}cyclopropanecarboxylate ESI (+) MS: m/z 258 (MH+).

EXAMPLE 9

Preparation of 5-isopropylpiperidine-2,4dione

Crude ethyl 2-{[(3-ethoxy-3-oxopropanoyl)amino]-methyl}-3-methylbutanoate (8.35 g, 30.55 mmol) was dissolved in 215 mL of dry toluene and heated to 100° C. 6.9 mL of sodium methoxide 30 wt. % solution in methanol were added (36 mmol) and the reaction mixture was refluxed for 4 hours. After cooling at room temperature, the organic phase was washed with water (×2). The aqueous layers were collected, acidified (10% HCl) and extracted with DCM (×4). The organic layers were collected and evaporated to dryness. The crude was treated with 250 mL of 10% AcOH in water and refluxed for 3 hours. The reaction mixture was neutralized with NaHCO₃ (~pH 7) and extracted with DCM (×5). The organic layers were collected, dried (Na₂SO₄), filtered and evaporated to dryness. Column chromatography (DCM/EtOH=97/3) afforded 2.35 g of target product (1 5.14 mmol, 49.6% yield).

1H NMR (400 MHz, DMSO-D6) δ ppm 0.85 (d, J=6.83 Hz, 3H) 0.94 (d, J=6.95 Hz, 3H) 2.07-2.17 (m, 1H) 2.25-2.33 (m, 1H) 3.09-3.41 (m, 4H) 8.03 (s, 1H) ESI (+) MS: m/z 156 (MH+).

By working in an analogous way and by starting from the suitable aminoester derivative, the following compounds were prepared:

5-sec-butylpiperidine-2,4dione $^1$H NMR (DMSO-d$_6$/400 MHz) δ ppm 0.87 (m, 6H) 1.36 (m, 2H) 1.95 (m, 1H) 2.35 (m, 1H) 3.34 (m, 4H), 8.02 (s, 1H) ESI (+) MS: m/z 170 (MH+).

5-azaspiro[2.5]octane-6,8-dione

1H NMR (400 MHz, DMSO-D6) δ ppm 0.95-1.02 (m, 2H) 1.09-1.15 (m, 2H) 3.33 (s, 2H) 3.42 (s, 2H) 8.22 (s, 1H) ESI (+) MS: m/z 140 (MH+).

5,5-diethylpiperidine-2,4dione

1H NMR (400 MHz, DMSO-D6) δ ppm 0.77 (t, J=7.56 Hz, 6H) 1.46 (q, J=7.68 Hz, 4H) 3.23 (d, J=3.78 Hz, 2H) 3.26 (s, 2H) 7.98 (s, 1H)

EXAMPLE 10

6-Benzylpiperidine-2,4-dione

A mixture of beta-homophenylalanine (9.1 g, 50.94 mmol), di-tert-butyl dicarbonate (12.2 g, 56.1 mmol), dioxane (180 mL), water (18 mL) and triethylamine (8.5 mL) was stirred at RT overnight. After concentration and multiple strippings with toluene, 3-[(tert-butoxycarbonyl)amino]-4-phenylbutanoic acid was obtained as an oil and used directly in the next step. It was dissolved in dry dichloromethane (370 mL), Meldrum acid (8.1 g, 56.1 mmol) and DMAP (9.7 g, 79 mmol) were added to it, the mixture was cooled to −5° C. and dicyclohexylcarbodiimide (12.6 g, 61 mmol) was added. After addition the reaction mixture was kept in refrigerator overnight. The precipitate was filtered off and washed with dichloromethane. The filtrate was diluted with ethylacetate, washed in sequence with 10% aq KHSO$_4$, water, brine then concentrated to yield crude tert-butyl 1-benzyl-3-(2,2-dimethyl-4,6-dioxo-1,3-dioxan-5-yl)-3-oxopropylcarbamate that was dissolved in ethylacetate (250 mL) and refluxed 2 h. After concentration and treatment with diisopropylether the crystallized compound was filtered and washed to give tert-butyl 2-benzyl-4,6-dioxopiperidine-1-carboxylate as a white powder in 75% overall yield.

The t-butoxycarbonyl group could be removed by acidic treatment (4M HCl in dioxane) at RT.

1H NMR (400 MHz, DMSO-D6) δ ppm 2.32 (dd, J=15.73, 8.17 Hz, 1H) 2.42 (dd, J=16.34, 4.76 Hz, 1H) 2.66-2.74 (m, 1H) 2.87-3.02 (m, 2H) 3.25-3.40 (m, 1H) 3.84-3.93 (m, 1H) 7.20-7.36 (m, 5H) 8.14 (s, 1H).

By working in an analogous way the following compounds were also obtained:

6-isopropylpiperidine-2,4-dione

ESI (+) MS: m/z 156 (MH+).

6-methylpiperidine-2,4-dione

ESI (+) MS: m/z 128 (MH+).

5,5-dimethylpiperidine-2,4-dione

1H NMR (300 MHz, DMSO-D6) δ ppm 1.0 (s, 6H) 3.15 (s, 2H) 3.25 (s, 2H) 8.0 (s, 1H).

6-(2-phenylethyl)piperidine-2,4-dione

ESI (+) MS: m/z 218 (MH+).

EXAMPLE 11

Preparation of 5-benzylypiperidine-2,4-dione

To a solution of tert-butyl 2,4-dioxopiperidine-1-carboxylate (324 mg, 1.5 mmol) in dry THF (10 mL), cooled to −20° C. under nitrogen, lithium bis(trimethylsilyl)amide (LiHMDS) (4 mL of 1 M solution in THF) was added dropwise. After 20 min stirring, 3.0 eq of benzyl bromide were added and the solution was stirred at −20° C. for 2 hours. The reaction mixture was poured into 5% aq KHSO$_4$ and extracted with DCM (×2). To the collected (200 mL) organic layers, 20 mL of TFA were added and the resulting solution was stirred at room temperature for 2 hours. After evaporation, the residue was purified by column chromatography (hexane/EtOAc 1:2) affording 150 mg of target product (0.74 mmol, 49%).

1H NMR (400 MHz, DMSO-D6) δ ppm 2.81 (m, 1H), 3.12 (m, 2H) 3.34 (m, 4H), 7.23-7.30 (m, 5H), 7.99 (s, 1H) ESI (+) MS: m/z 204 (MH+).

By working in an analogous way and by using the suitable alkyl halide, the following compounds were prepared:

5-isobutylpiperidine-2,4-dione

1H NMR (400 MHz, DMSO-D6) δ ppm 0.88 (m, 6H), 1.16 (m, 1H), 1.53 (m, 1H), 1.61 (m, 1H), 3.08 (m, 1H) 3.20-3.40 (m, 4H), 8.03 (s, 1H) ESI (+) MS: m/z 170 (MH+).

5-ethylpiperidine-2,4-dione

1H NMR (400 MHz, DMSO-D6) δ ppm 0.89 (t, J=7.56, 3H), 1.35 (m, 1H), 1.69 (m, 1H), 2.39 (m, 1H), 3.14-3.38 (m, 4H), 8.05 (s, 1H) ESI (+) MS: m/z 142 (MH+).

EXAMPLE 12

Preparation of tert-butyl 5-ethyl-2,4-dioxopiperidine-1-carboxylate

To a solution of tert-butyl 2,4-dioxopiperidine-1-carboxylate (1.92 g, 9.0 mmol), in dry THF (65 mL) and cooled to −20° C. under nitrogen, lithium bis(trimethylsilyl)amide (LiHMDS) (27 mL of 1 M solution in THF) was added dropwise. After 20 min stirring, 2.53 mL (4.9 g, 31.3 mmol) of iodoethane were added and the solution was stirred at −20° C. for 2 hours. The reaction mixture was poured in 5% aq KHSO$_4$ and extracted with DCM (×2). The collected organic layers were washed with water, dried over Na$_2$SO$_4$ and evaporated to dryness. The residue was purified by column chromatography (n-Hexane/EtOAc 1:1) affording 1.4 g of target product (5.8 mmol, 64%). ESI (+) MS: m/z 242 (MH+).

By working in an analogous way and by using 1-iodo-3-methylbutane, the following compound was prepared:

tert-butyl 5-isobutyl-2,4-dioxopiperidine-1-carboxylate ESI (+) MS: m/z 270 (MH+).

EXAMPLE 13

2-pyrimidin-4-yl-1,5,6,7-tetrahydro-4H-pyrrolo[3,2-c]pyridin-4-one hydrochloride 2-Bromo-1-pyrimidin-4-ylethanone hydrobromide (67 mg, 0.239 mmols), piperidine-2,4-dione (50 mg, 0.358 mmols) and ammonium acetate (74 mg, 0.957 mmols) were dissolved in anhydrous ethanol (1 mL) and stirred at r.t. overnight. The reaction mixture was concentrated to dryness under reduced pressure and the residue was taken up with water (1 mL) and filtered; the solid was washed with cold water and dried.

To the obtained brown solid (30 mg) dissolved in MeOH (15 mL), 4N HCl in dioxane (0.5 mL) was added and the mixture was stirred for 30 minutes and then concentrated under reduced pressure to half of the volume.

The obtained precipitate was filtered, washed with ethyl acetate and dried to give the title compound as a yellow solid (31 mg, Y=52%).

$^1$H NMR (DMSO-$d_6$/400 MHz) δ ppm 2.87 (t, 2H, J=6.83), 3.44 (t, 2H, J=6.83), 7.19 (bs, 1H), 7.37 (s, 1H), 7.89 (d, 1H, J=5.85), 8.68 (d, 1H, J=5.85), 9.10 (s, 1H)

By working in an analogous way the following compounds were also obtained:

2-(2-aminopyrimidin-4-yl)-1,5,6,7-tetrahydro-4H-pyrrolo[3,2-c]pyridin-4-one hydrochloride $^1$H NMR (DMSO-$d_6$/400 MHz) δ ppm 2.91 (t, 2H, J=6.71), 3.36 (t, 2H, J=6.71), 7.27 (d, 1H, J=6.70), 7.29 (bs, 1H), 7.46 (s, 1H), 7.86 (br, 2H), 8.21 (d, 2H, J=6.70).

6,6-dimethyl-2-(2-aminopyrimidin-4-yl)-1,5,6,7-tetrahydro-4H-pyrrolo[3,2-c]pyridin-4-one hydrochloride $^1$H NMR (DMSO-$d_6$/400 MHz): δ ppm 1.3 (sc, J=2.7, 0.9, 0.5 Hz, 3H) 1.5 (sc, J=2.7, 0.9, 0.5 Hz, 3H) 2.5 (sc, J=15.6, 1.5, 0.9, 0.5 Hz, 1H) 2.6 (sc, J=15.6, 1.5, 0.9, 0.5 Hz, 1H) 7.5 (sc, J=0.9 Hz, 1H) 7.7 (sc, J=4.8 Hz, 1H) 8.2 (sc, J=4.8 Hz, 1H) 9.2 (sc, 1H).

2-(2-phenylaminopyrimidin-4-yl)-1,5,6,7-tetrahydro-4H-pyrrolo[3,2-c]pyridin-4-one 1H NMR (400 MHz, Solvent) δ ppm 2.7 (sc, J=17.1, 6.2, 5.1, 1.5, 0.9 Hz, 1H) 2.8 (sc, J=17.1, 6.3, 5.1, 1.5, 0.9 Hz, 1H) 3.5 (sc, J=12.2, 6.2, 5.1, 2.5 Hz, 1H) 3.5 (sc, J=12.2, 6.3, 5.1, 2.5 Hz, 1H) 6.9 (sc, J=7.5, 1.2 Hz, 1H) 7.3 (sc, J=8.1, 7.5, 1.6, 0.4 Hz, 1H) 7.3 (sc, J=8.1, 7.5, 1.6, 0.4 Hz, 1H) 7.6 (sc, J=0.9 Hz, 1H) 7.6 (sc, J=8.1, 2.5, 1.2, 0.4 Hz, 1H) 7.6 (sc, J=8.1, 2.5, 1.2, 0.4 Hz, 1H) 7.7 (sc, J=4.8 Hz, 1H) 8.4 (sc, J=4.8 Hz, 1H).

2-(2-phenylaminopyrimidin-4-yl)-7-phenyl-1,5,6,7-tetrahydro-4H-pyrrolo[3,2-c]pyridin-4-one hydrochloride 1H NMR (400 MHz, Solvent) δ ppm 3.7 (sc, J=1 3.0, 8.0, 4.0 Hz, 1H) 3.8 (sc, J=8.0, 6.0, 1.5, 0.9, 0.6 Hz, 1H) 3.9 (sc, J=13.0, 6.0, 3.0 Hz, 1H) 6.9 (sc, J=7.5, 1.2 Hz, 1H) 7.0 (sc, J=7.3, 7.1, 1.4, 1.0 Hz, 1H) 7.0 (sc, J=7.3, 7.1, 1.4, 1.0 Hz, 1H) 7.2 (sc, J=7.1, 1.2 Hz, 1H) 7.3 (sc, J=8.1, 7.5, 1.6, 0.4 Hz, 1H) 7.3 (sc, J=8.1, 7.5, 1.6, 0.4 Hz, 1H) 7.4 (sc, J=7.3, 1.2, 1.2, 1.0, 0.6 Hz, 1H) 7.4 (sc, J=7.3, 1.2, 1.2, 1.0, 0.6 Hz, 1H) 7.6 (sc, J=0.9 Hz, 1H) 7.6 (sc, J=8.1, 2.5, 1.2, 0.4 Hz, 1H) 7.6 (sc, J=8.1, 2.5, 1.2, 0.4 Hz, 1H) 7.7 (sc, J=4.8 Hz, 1H) 8.4 (sc, J=4.8 Hz, 1H) 9.2 (sc, 1H).

2-(9H-purin-6-yl)-1,5,6,7-tetrahydro-4H-pyrrolo[3,2-c]pyridin-4-one hydrochloride $^1$H NMR (DMSO-$d_6$/400 MHz) δ ppm 2.91 (t, 2H, J=6.83), 3.42 (t, 2H, J=6.83), 7.16 (br, 1H), 7.77 (s, 1H), 8.59 (s, 1H), 8.80 (s, 1H), 12.26 (bs, 1H).

7-phenyl-2-pyrimidin-4-yl-1,5,6,7-tetrahydro-4H-pyrrolo[3,2-c]pyridin-4-one hydrochloride 1H NMR (400 MHz, Solvent) δ ppm 3.7 (sc, J=13.0, 8.0, 4.0 Hz, 1H) 3.8 (sc, J=8.0, 6.0, 1.5, 0.9, 0.6 Hz, 1H) 3.9 (sc, J=13.0, 6.0, 3.0 Hz, 1H) 7.0 (sc, J=7.3, 7.1, 1.4, 1.0 Hz, 1H) 7.0 (sc, J=7.3, 7.1, 1.4, 1.0 Hz, 1H) 7.2 (sc, J=7.1, 1.2 Hz, 1H) 7.4 (sc, J=7.3, 1.2, 1.2, 1.0, 0.6 Hz, 1H) 7.4 (sc, J=7.3, 1.2, 1.2, 1.0, 0.6 Hz, 1H) 7.5 (sc, J=0.9 Hz, 1H) 7.8 (sc, J=4.8, 1.0 Hz, 1H) 8.9 (sc, J=4.8, 0.5 Hz, 1H) 9.0 (sc, J=1.0, 0.5 Hz, 1H) 9.2 (sc, 1H).

2-(2-aminopyrimidin-4-yl)-7-phenyl-1,5,6,7-tetrahydro-4H-pyrrolo[3,2-c]pyridin-4-one hydrochloride 1H NMR (400 MHz, Solvent) δ ppm 3.7 (sc, J=13.0, 8.0, 4.0 Hz, 1H) 3.8 (sc, J=8.0, 6.0, 1.5, 0.9, 0.6 Hz, 1H) 3.9 (sc, J=13.0, 6.0, 3.0 Hz, 1H) 7.0 (sc, J=7.3, 7.1, 1.4, 1.0 Hz, 1H) 7.0 (sc, J=7.3, 7.1, 1.4, 1.0 Hz, 1H) 7.2 (sc, J=7.1, 1.2 Hz, 1H) 7.4 (sc, J=7.3, 1.2, 1.2, 1.0, 0.6 Hz, 1H) 7.4 (sc, J=7.3, 1.2, 1.2, 1.0, 0.6 Hz, 1H) 7.5 (sc, J=0.9 Hz, 1H) 7.7 (sc, J=4.8 Hz, 1H) 8.2 (sc, J=4.8 Hz, 1H) 9.2 (sc, 1H);

7-phenyl-2-(9H-purin-6-yl)-1,5,6,7-tetrahydro-4H-pyrrolo[3,2-c]pyridin-4-one hydrochloride $^1$H NMR (DMSO-$d_6$/400 MHz) δ ppm 3.93 (dd,2H, J=5.37, 12.80), 4.89 (m, 1H), 7.18 (d, 2H), 7.25 (t, 1H), 7.32 (t, 2H), 7.85 (s, 1H), 8.60 (s, 1H), 8.78 (s, 1H), 12.27 (bs, 1H).

2-(2-aminopyrimidin-4-yl)-6-isopropyl-1,5,6,7-tetrahydro-4H-pyrrolo[3,2-c]pyridin-4-one hydrochloride 1H NMR (400 MHz, DMSO-D6) δ ppm 0.92 (dd, J=4.15, 6.83 Hz, 6H) 1.86 (m, 1H) 2.79 (dd, J=9.39, 16.95 Hz, 1H) 2.92 (dd, J=0.48, 19.90 Hz, 1H) 3.52 (m, 1H) 7.26 (bs, 1H) 7.31 (d, J=6.83 Hz, 1H) 7.52 (bs, 1H) 8.21 (d, J=6.71 Hz, 1H) 12.32 (bs, 1H)

2-(2-aminopyrimidin-4-yl)-7-methyl-1,5,6,7-tetrahydro-4H-pyrrolo[3,2-c]pyridin-4-one hydrochloride 1H NMR (400 MHz, DMSO-D6) δ ppm 1.29 (d, J=6.58 Hz, 3H) 3.06-3.24 (m, 2H) 3.41-3.56 (m, 1H) 7.30 (s, 1H) 7.35 (d, J=6.83 Hz, 1H) 7.51 (s, 1H) 8.03 (s, 2H) 8.23 (d, J=6.71 Hz, 1H) 12.24 (s, 1H)

The racemate, as Boc derivative, was subjected to chiral separation so to obtain the pure enantiomers. Chiral chromatography was performed on CHIRALCELL® OJ (5×50 cm). Mobile phase was n-Hex/EtOH/MeOH 70:23:7.

Analytical conditions, as hydrochloride: Chiralcell® OJ column, with precolumn, mobile phase n-Hex/EtOH 80:20.

(7R or 7S)-2-(2-aminopyrimidin-4-yl)-7-methyl-1,5,6,7-tetrahydro-4H-pyrrolo[3,2-c]pyridin-4-one RT 19.3 min; e.e. 98.7%

(7R or 7S)-2-(2-aminopyrimidin-4-yl)-7-methyl-1,5,6,7-tetrahydro-4H-pyrrolo[3,2-c]pyridin-4-one RT 24.1 min; e.e. 99.8%

2-(2-aminopyrimidin-4-yl)-6-methyl-1,5,6,7-tetrahydro-4H-pyrrolo[3,2-c]pyridin-4-one hydrochloride 1H NMR (400 MHz, DMSO-D6) δ ppm 1.24 (d, J=6.34 Hz, 3H) 2.65 (dd, J=16.71, 10.12 Hz, 1H) 3.01 (dd, J=16.58, 5.00 Hz, 1H) 3.73-3.85 (m, 1H) 7.30 (s, 1H) 7.31 (d, J=7.19 Hz, 1H) 7.52 (d, J=2.07 Hz, 1H) 8.03 (s, 2H) 8.21 (d, J=6.71 Hz, 1H) 12.34 (s, 1H)

2-(2-aminopyrimidin-4-yl)-7,7-dimethyl-1,5,6,7-tetrahydro-4H-pyrrolo[3,2-c]pyridin-4-one hydrochloride 1H NMR (500 MHz, DMSO-D6) δ ppm 1.37 (s, 6H) 3.20 (s, 2H) 7.39-7.43 (m, 1H) 7.46 (d, J=6.70 Hz, 1H) 7.52 (s, 1H) 8.16 (s, 2H) 8.28 (d, J=6.70 Hz, 1H) 12.20 (s, 1H)

2-(2-aminopyrimidin-4-yl)-6-isobutyl-1,5,6,7-tetrahydro-4H-pyrrolo[3,2-c]pyridin-4-one hydrochloride 1H NMR (400 MHz, DMSO-D6) δ ppm 0.81-0.97 (m, 6H); 1.27-1.42 (m, 1H); 1.42-1.58 (m, 1H); 1.64-1.81 (m, 1H); 2.70 (dd, J=16.58, 8.41 Hz, 1H); 3.04 (dd, J=16.58, 5.24 Hz, 1H); 3.63-3.80 (m, 1H); 7.29 (s, 1H); 7.31 (d, J=6.71 Hz, 1H); 7.51 (s, 1H); 8.08 (s, 2H); 8.21 (d, J=6.71 Hz, 1H); 12.35 (s, 1H)

2-(2-aminopyrimidin-4-yl)-7,7-diethyl-1,5,6,7-tetrahydro-4H-pyrrolo[3,2-c]pyridin-4-one hydrochloride 1H NMR (400 MHz, DMSO-D6) δ ppm 0.80 (t, J=7.44 Hz, 6H) 1.73-1.85 (m, 4H) 3.27 (d, J=2.56 Hz, 2H) 7.31 (s, 1H) 7.37-7.43 (m, 1H) 7.46 (s, 1H) 7.91 (s, 2H) 8.24 (d, J=6.58 Hz, 1H) 11.98 (s, 1H)

2-(2-aminopyrimidin-4-yl)-7-isopropyl-1,5,6,7-tetrahydro-4H-pyrrolo[3,2-c]pyridin-4-one 1H NMR (400 MHz, DMSO-D6) δ ppm 0.91 (d, J=6.95 Hz, 6H) 1.07 (t, J=6.95 Hz, 1H) 1.96-2.10 (m, 1H) 2.66-2.74 (m, 1H) 3.40-3.54 (m, 1H) 6.28-6.39 (m, 2H) 6.95 (d, J=5.37 Hz, 1H) 6.97 (s, 1H) 7.03 (d, J=2.19 Hz, 1H) 8.16 (d, J=5.24 Hz, 1H) 11.64 (s, 1H)

EXAMPLE 14

2-(2-Amino-pyrimidin-4-yl)-3-iodo-1,5,6,7-tetrahydro-pyrrolo[3,2-c]pyridin-4-one KOH (61 mg, 1.09 mmol) was added to a solution of 2-(2-amino-pyrimidin-4-yl)-1,5,6,7-tertrahydro-pyrrolo[3,2-c]pyridin-4-one (100 mg, 0.44 mmol) in DMF (5 ml). A solution of iodine (115 mg, 0.45 mmol) in DMF (2 ml) was added. After 30 min the reaction mixture was poured onto ice water (containing 0.5 ml NH₃ and 25 mg K₂S₂O₅). The yellow precipitate was filtered, washed with cold water and dried. The compound was purified by flash chromatography (DCM-MeOH-30% NH₄OH, 95:5:0.5) to give the product as a yellow solid (22 mg, 14% yield).

$^1$H NMR (400 MHz, DMSO-d6) δ ppm 2.87 (t, J=6.77 Hz, 2H), 3.23-3.44 (m, 2H), 6.41 (s, 2H), 7.13 (t, J=2.68 Hz, 1H), 7.51 (d, J=5.37 Hz, 1H), 8.29 (d, J=5.24 Hz, 1H), 12.03 (s, 1H).

EXAMPLE 15

2-[2-(Cyclohexylmethyl-amino)-pyrimidin-4-yl-]1,5,6,7-tetrahydro-pyrrolo [3,2-c]pyridin-4-one 2-(2-Amino-pyrimidin-4-yl)-1,5,6,7-tetrahydro-pyrrolo[3,2-c]pyridin-4-one (140 mg, 0.61 mmol), trifluoroacetic acid (565 μl, 7.33 mmol), and cyclohexanecarbaldehyde (151 μl, 1.25 mmol) were mixed in DMF (10 ml). Sodium triacetoxyborohydride (390 mg, 1.84 mmol) was added to the above solution and the reaction mixture stirred at room temperature under N₂ for 20 h. Additional cyclohexanecarbaldehyde (151 μl, 1.25 mmol) and sodium triacetoxyborohydride (390 mg, 1.84 mmol) were added and the reaction mixture was stirred 20 hours longer. The reaction was quenched with 0.33N NaOH (50 ml), and the product was extracted with DCM (50 ml). The DCM extract was dried (MgSO₄), and the solvent was evaporated. The residue was purified by flash chromatography (DCM-MeOH, 95:5) to give the product as a beige solid (80 mg, 40% yield).

$^1$H NMR (400 MHz, DMSO-d6) δ ppm 0.87-1.29 (m, 5H), 1.43-1.85 (m, 6H), 2.87 (t, J=6.77 Hz, 2H), 3.18-3.31 (m, 2H), 3.38-3.49 (m, 2H), 6.67-6.95 (m, 1H), 6.85 (d, J=5.24 Hz, 1H), 7.03 (d, J=2.19 Hz, 1H), 7.06 (t, J=2.07 Hz, 1H), 8.15 (d, J=5.12 Hz, 1H), 11.65 (s, 1H). Analogously the following products can be prepared starting from the corresponding aldehyde:

2-(2-Propylamino-pyrimidin-4-yl)-1,5,6,7-tetrahydro-pyrrolo[3,2-c]pyridin-4-one $^1$H NMR (400 MHz, DMSO-d6) δ ppm 0.93 (t, J=7.38 Hz, 3H), 1.51-1.64 (m, 2H), 2.87 (t, J=6.89 Hz, 2H), 3.34-3.48 (m, 4H), 6.81 (s, 1H), 6.86 (d, J=5.24 Hz, 1H), 7.03 (d, J=2.32 Hz, 1H), 7.05 (t, J=2.07 Hz, 1H), 8.16 (d, J=5.24 Hz, 1H), 11.66 (s, 1H).

2-(2-Dipropylamino-pyrimidin-4-yl)-1,5,6,7-tetrahydro-pyrrolo[3,2-c]pyridin-4-one $^1$H NMR (400 MHz, DMSO-d6) δ ppm 0.90 (t, J=7.38 Hz, 6H), 1.53-1.70 (m, 4H), 2.89 (t, J=6.77 Hz, 2H), 3.38-3.49 (m, 2H), 3.59 (s, 4H), 6.86 (d, J=5.24 Hz, 1H), 7.05 (d, J=2.44 Hz, 1H), 7.06-7.07 (m, 1H) 8.22 (d, J=5.12 Hz, 1H), 11.62 (s, 1H).

2-(2-Isobutylamino-pyrimidin-4-yl)-1,5,6,7-tetrahydro-pyrrolo[3,2-c]pyridin-4-one $^1$H NMR (400 MHz, DMSO-d6) δ ppm 0.93 (d, J=6.71 Hz, 6H), 1.81-1.95 (m, 1H), 2.87 (t, J=6.83 Hz, 2H), 3.24 (s, 2H), 3.41 (td, J=6.98, 2.38 Hz, 2H), 6.71-6.94 (m, 1H), 6.87 (d, J=5.24 Hz, 1H), 7.04 (d, J=2.32 Hz, 1H), 7.06 (t, J=2.38 Hz, 1H), 8.16 (d, J=5.12 Hz, 1H), 11.66 (s, 1H).

2-{2-[(Furan-2-ylmethyl)-amino]-pyrimidin-4-yl}-1,5,6,7-tetrahydro-pyrrolo[3,2-c]pyridin-4-one $^1$H NMR (400 MHz, DMSO-d6) δ ppm 2.87 (t, J=6.83 Hz, 2H), 3.19-3.48 (m, 2H), 4.66 (d, J=3.66 Hz, 2H), 6.28

(d, J=2.68 Hz, 1H), 6.38 (dd, J=3.17, 1.83 Hz, 1H), 6.94 (d, J=5.24 Hz, 1H), 7.03-7.10 (m, 2H), 7.28 (s, 1H), 7.56 (dd, J=1.71, 0.85 Hz, 1H), 8.19 (d, J=5.24 Hz, 1H), 11.75 (s, 1H).

N-(4-{[4-(4-Oxo-4,5,6,7-tetrahydro-1H-pyrrolo[3,2-c]pyridin-2-yl)-pyrimidin-2-ylamino]-methyl}-phenyl)acetamide $^1$H NMR (400 MHz, DMSO-d6) δ ppm 2.03 (s, 3H), 2.91 (t, 2H), 3.38 (m, 2H), 4.73 (bs, 2H), 7.1-7.45 (m, 7H), 7.53 (m, 2H), 8.17 (d, 1H), 12.0 (s, 1H).

2-(2-Benzylamino-pyrimidin-4-yl)-1,5,6,7-tetrahydro-pyrrolo[3,2-c]pyridin-4-one $^1$H NMR (500 MHz, DMSO-d6) δ ppm 2.87 (t, J=6.85 Hz, 2H), 3.42 (td, J=6.85, 2.44 Hz, 2H), 4.68 (s, 2H), 6.92 (d, J=5.18 Hz, 1H), 7.07 (d, J=2.28 Hz, 1H), 7.08 (t, J=2.51 Hz, 1H), 7.21-7.26 (m, 1H), 7.27-7.48 (m, 1H), 7.32 (t, J=7.54 Hz, 2H), 7.39 (d, J=7.76 Hz, 2H), 8.19 (d, J=5.18 Hz, 1H), 11.73 (s, 1H).

EXAMPLE 16

N-[4-(4-oxo-4,5,6,7-tetrahydro-1H-pyrrolo[3,2-c]pyridin-2-yl)pyrimidin-2-yl]benzamide To a solution of 2-(2-Benzoylamino-pyrimidin-4-yl)-4-oxo-1,4,6,7-tetrahydro-pyrrolo[3,2-c]pyridine-5-carboxylic acid tert-butyl ester in THF was added HCl 4N in dioxane and the reaction was left under stirring at room temperature for 2h. Solvent evaporation gave the desired product as a solid.

$^1$H-NMR (DMSO-d$_6$) δ ppm 1.45 (2H), 3.44 (2H), 7.22 (1H), 7.36 (1H), 7.57 (2H), 7.64 (2H), 8.03 (2H), 8.59 (1H), 11.26 (1H), 12.13 (1H).

2-(2-Benzoylamino-pyrimidin-4-yl)-4-oxo-1,4,6,7-tetrahydro-pyrrolo[3,2-c]pyridine-5-carboxylic acid tert-butyl ester To a mixture of 2-(2-Amino-pyrimidin-4-yl)-4-oxo-1,4,6,7-tetrahydro-pyrrolo[3,2-c]pyridine-5-carboxylic acid tert-butyl ester and Et$_3$N (4 eq.) in dry THF, PhCOCl (2 eq.) was added and the mixture was stirred at room temperature under argon overnight. Thus NaOH(1N) was added; after 30' the solvent was evaporated and the residue was dissolved in water and the aqueous phase was extracted with AcOEt (2×). The organic phase was then washed with aq. NH$_4$Cl and dried over Na$_2$SO$_4$. After solvent evaporation the crude product was purified by flash chromatography (CH$_2$Cl$_2$:MeOH 97:3) to give the pure product as a solid.

$^1$H-NMR (400 MHz, DMSO-d$_6$) δ ppm 1.49 (s, 9H), 2.98 (2H), 3.98 (2H), 7.35 (1H), 7.51-7.66 (m, 4H), 8.00 (2H), 10.82 (1H), 12.11 (1H).

Analogously the following products can be prepared starting from the corresponding acylating agent.

2-methyl-N-[4-(4-oxo-4,5,6,7-tetrahydro-1H-pyrrolo[3,2-c]pyridin-2-yl)pyrimidin-2-yl]propanamide hydrochloride $^1$H-NMR (400 MHz, DMSO-d$_6$): δ ppm 1.15 (6H, d), 2.93 (3H, m), 3.43 (2H), 7.25 (1H), 7.36 (1H, s) 7.58 (1H), 8.51 (1H), 11.03 (1H), 12.16 (1H).

N-[4-(4-oxo-4,5,6,7-tetrahydro-1H-pyrrolo[3,2-c]pyridin-2-yl)pyrimidin-2-yl]thiophene-2-carboxamide hydrochloride $^1$H-NMR (400 MHz, DMSO-d$_6$): δ ppm 2.91 (2H), 3.44 (2H), 7.22 (1H), 7.27 (1H), 7.36 (1H), 7.63 (1H), 7.97 (1H), 8.22 (1H), 8.59 (1H), 11.33 (1H), 12.10 (1H).

N-[4-(4-oxo-4,5,6,7-tetrahydro-1H-pyrrolo[3,2-c]pyridin-2-yl)pyrimidin-2-yl]-2-phenylacetamide hydrochloride $^1$H-NMR (400 MHz, DMSO-d$_6$): δ ppm 2.90 (2H), 3.42 (2H), 3.93 (2H, s), 7.21 (1H), 7.31 (5H) 7.34 (1H), 7.54 (1H), 8.51 (1H), 11.03 (1H), 12.06 (1H).

N-[4-(4-oxo-4,5,6,7-tetrahydro-1H-pyrrolo[3,2-c]pyridin-2-yl)pyrimidin-2-yl]acetamide hydrochloride $^1$H-NMR (400 MHz, DMSO-d$_6$): δ ppm 2.31 (3H, s), 2.92 (2H, t), 3.51 (2H), 7.26 (1H), 7.37 (1H, s) 7.60 (1H), 8.50 (1H), 11.11 (1H), 12.22 (1H).

ethyl 4-(4-oxo-4,5,6,7-tetrahydro-1H-pyrrolo[3,2-c]pyridin-2-yl)pyrimidin-2-ylcarbamate $^1$H NMR (400 MHz, DMSO-d6) δ ppm 1.26 (t, 3H), 2.88 (t, 2H), 3.2-3.5 (m, 2H), 4.17 (q, 2H), 7.12 (t, 1H), 7.2 (d, 1H), 7.4 (d, 1H), 8.48 (d, 1H), 10.05 (s, 1H), 11.80 (s, 1H).

The invention claimed is:

1. A compound of formula (I)

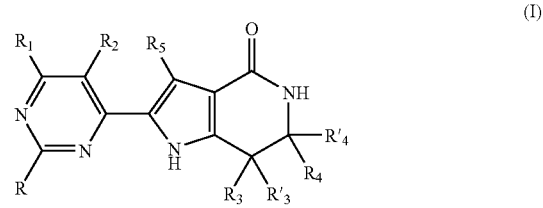

wherein

R is a hydrogen atom or a group selected from amino, arylamino, optionally substituted $C_1$-$C_6$ alkylamino, optionally substituted arylalkylamino, heteroarylalkylamino, $C_1$-$C_6$ dialkylamino and acylamino;

$R_1$ and $R_2$ are, each independently, a hydrogen or halogen atom, a straight or branched $C_1$-$C_6$ alkyl group, an amino or arylamino group;

$R_3$, $R'_3$, $R_4$ and $R'_4$ are, each independently, a hydrogen atom or a group selected from straight or branched $C_1$-$C_6$ alkyl, $C_3$-$C_6$ cycloalkyl, heterocyclyl, aryl, cycloalkyl-alkyl, heterocyclyl-alkyl or aryl-alkyl; or $R_3$ and $R_3'$ or $R_4$ and $R_4'$, taken together, form a $C_3$-$C_6$ cyclic alkyl group;

$R_5$ is a hydrogen or halogen atom or a straight or branched $C_1$-$C_6$ alkyl group and pharmaceutically acceptable salts thereof.

2. A compound of formula (I) according to claim 1 wherein R is hydrogen, amino or phenylamino; $R_1$ and $R_2$ are both hydrogen atoms.

3. A compound of formula (I) according to claim 1 wherein $R_3$ and $R'_3$ are both hydrogen atoms or one of them is a phenyl group and the remaining one is a hydrogen atom.

4. A compound of formula (I) according to claim 1 wherein $R_4$ and $R'_4$ are both hydrogen atoms or both methyl groups.

5. A compound of formula (I) according to claim 1 wherein $R_5$ is a hydrogen atom.

6. A compound of formula (I) according to claim 1, optionally in the form of a pharmaceutically acceptable salt thereof, selected from the group consisting of:
   2-(2-aminopyrimidin-4-yl)-1,5,6,7-tetrahydro-4H-pyrrolo[3,2-c]pyridin-4-one hydrochloride;
   2-(2-aminopyrimidin-4-yl)-7-phenyl-1,5,6,7-tetrahydro-4H-pyrrolo[3,2-c]pyridin-4-one hydrochloride; 2-(2-phenylaminopyrimidin-4-yl)-1,5,6,7-tetrahydro-4H-pyrrolo[3,2-c]pyridin-4-one hydrochloride;
   2-(9H-purin-6-yl)-1,5,6,7-tetrahydro-4H-pyrrolo[3,2-c]pyridin-4-one hydrochloride; 2-pyrimidin-4-yl-1,5,6,7-tetrahydro-4H-pyrrolo[3,2-c]pyridin-4-one hydrochloride; 7-phenyl-2-(9H-purin-6-yl)-1,5,6,7-tetrahydro-4H-pyrrolo[3,2-c]pyridin-4-one hydrochloride;
   2-(2-aminopyrimidin-4-yl)-6,6-dimethyl-1,5,6,7-tetrahydro-4H-pyrrolo[3,2-c]pyridin-4-one hydrochloride;
   7-phenyl-2-pyrimidin-4-yl-1,5,6,7-tetrahydro-4H-pyrrolo[3,2-c]pyridin-4-one hydrochloride;
   2-(2-anilinopyrimidin-4-yl)-7-phenyl-1,5,6,7-tetrahydro-4H-pyrrolo[3,2-c]pyridin-4-one hydrochloride;
   2-(2-aminopyrimidin-4-yl)-6-isopropyl-1,5,6,7-tetrahydro-4H-pyrrolo[3,2-c]pyridin-4-one;
   2-(2-aminopyrimidin-4-yl)-7-methyl-1,5,6,7-tetrahydro-4H-pyrrolo[3,2-c]pyridin-4-one;
   2-(2-aminopyrimidin-4-yl)-6-methyl-1,5,6,7-tetrahydro-4H-pyrrolo[3,2-c]pyridin-4-one;
   2-(2-aminopyrimidin-4-yl)-7,7-dimethyl-1,5,6,7-tetrahydro-4H-pyrrolo[3,2-c]pyridin-4-one;
   2-(2-aminopyrimidin-4-yl)-6-isobutyl-1,5,6,7-tetrahydro-4H-pyrrolo[3,2-c]pyridin-4-one;
   (7R or 7S)-2-(2-aminopyrimidin-4-yl)-7-methyl-1,5,6,7-tetrahydro-4H-pyrrolo[3,2-c]pyridin-4-one;
   2-(2-aminopyrimidin-4-yl)-3-iodo-1,5,6,7-tetrahydro-4H-pyrrolo[3,2-c]pyridin-4-one;
   2-(2-aminopyrimidin-4-yl)-7,7-diethyl-1,5,6,7-tetrahydro-4H-pyrrolo[3,2-c]pyridin-4-one;
   2-{2-[(2-furylmethyl)amino]pyrimidin-4-yl}-1,5,6,7-tetrahydro-4H-pyrrolo[3,2-c]pyridin-4-one;
   N-[4-(4-oxo-4,5,6,7-tetrahydro-1H-pyrrolo[3,2-c]pyridin-2-yl)pyrimidin-2-yl]benzamide;
   2-(2-aminopyrimidin-4-yl)-7-isopropyl-1,5,6,7-tetrahydro-4H-pyrrolo[3,2-c]pyridin-4-one;
   2-[2-(benzylamino)pyrimidin-4-yl]-1,5,6,7-tetrahydro-4H-pyrrolo[3,2-c]pyridin-4-one;
   2-[2-(propylamino)pyrimidin-4-yl]-1,5,6,7-tetrahydro-4H-pyrrolo[3,2-c]pyridin-4-one;
   2-[2-(isobutylamino)pyrimidin-4-yl]-1,5,6,7-tetrahydro-4H-pyrrolo[3,2-c]pyridin-4-one;
   2-{2-[(cyclohexylmethyl)amino]pyrimidin-4-yl}-1,5,6,7-tetrahydro-4H-pyrrolo[3,2-c]pyridin-4-one;
   2-{2-[(2-furylmethyl)amino]pyrimidin-4-yl}-1,5,6,7-tetrahydro-4H-pyrrolo[3,2-c]pyridin-4-one and
   N-[4-({[4-(4-oxo-4,5,6,7-tetrahydro-1H-pyrrolo[3,2-c]pyridin-2-yl)pyrimidin-2-yl]amino}methyl)phenyl]acetamide trifluoroacetate.

7. A process for preparing the compounds of formula (I) and the pharmaceutically acceptable salts thereof, according to claim 1, which process comprises:
   a) halogenating a compound of formula (II) so as to obtain a compound of formula (III)

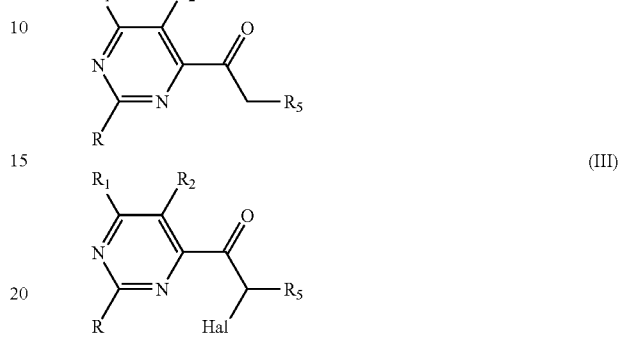

wherein $R_5$ is a hydrogen atom or a straight or branched $C_1$-$C_6$ alkyl group and Hal represents a halogen atom;
   b) reacting the compound of formula (III) with a compound of formula (IV)

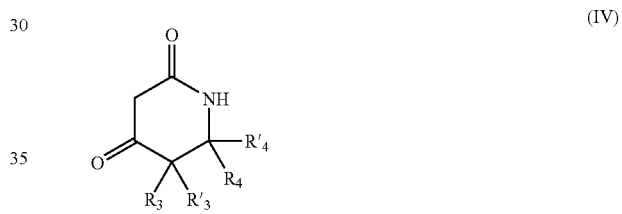

so as to obtain a compound of formula (I) and, optionally, converting it into another compound of formula (I) and/or into a pharmaceutically acceptable salt thereof.

8. The process according to claim 7 wherein step (a) is carried out by brominating or chlorinating the compound of formula (II).

9. The process according to claim 8 wherein, within the compound of formula (III), represents a bromine or chlorine atom.

10. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

11. A pharmaceutical composition according to claim 10 further comprising one or more chemotherapeutic agents.

12. A compound of formula (I) or a pharmaceutically acceptable salt thereof, as defined in claim 1, for use as a medicament.

* * * * *